United States Patent
Sambandan et al.

(10) Patent No.: US 10,213,780 B2
(45) Date of Patent: Feb. 26, 2019

(54) MULTIVALENCE SEMICONDUCTOR PHOTOCATALYTIC MATERIALS

(71) Applicant: NITTO DENKO CORPORATION, Osaka (JP)

(72) Inventors: Ekambaram Sambandan, Carlsbad, CA (US); Bin Zhang, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 15/510,621

(22) PCT Filed: Sep. 11, 2015

(86) PCT No.: PCT/US2015/049805
§ 371 (c)(1),
(2) Date: Mar. 10, 2017

(87) PCT Pub. No.: WO2016/040875
PCT Pub. Date: Mar. 17, 2016

(65) Prior Publication Data
US 2017/0291170 A1  Oct. 12, 2017

Related U.S. Application Data

(60) Provisional application No. 62/050,030, filed on Sep. 12, 2014.

(51) Int. Cl.
| | |
|---|---|
| *B01J 35/00* | (2006.01) |
| *B01J 37/08* | (2006.01) |
| *B01J 37/16* | (2006.01) |
| *B01J 21/06* | (2006.01) |
| *B01J 23/72* | (2006.01) |

(Continued)

(52) U.S. Cl.
CPC ............ *B01J 35/004* (2013.01); *A61L 9/18* (2013.01); *B01D 53/007* (2013.01);
(Continued)

(58) Field of Classification Search
None
See application file for complete search history.

(56) References Cited

U.S. PATENT DOCUMENTS

| | | | | |
|---|---|---|---|---|
| 4,387,359 A | * | 6/1983 | Tien | G01N 27/12 338/34 |
| 4,936,956 A | * | 6/1990 | Wrighton | B82Y 10/00 204/403.14 |

(Continued)

OTHER PUBLICATIONS

Huang et al, Highly aligned Cu2O, Cu2O/CuO, Cu2O/CuO/TiO2 and Cu2O/TiO2 nanowires arrays as photocathodes for water photoelectrolysis, journal of materials chemistry A, 1, pp. 2418-2425 (Year: 2013).*

(Continued)

*Primary Examiner* — Melvin C. Mayes
*Assistant Examiner* — Stefanie J Cohen
(74) *Attorney, Agent, or Firm* — K&L Gates LLP; Louis C. Cullman; Hal Gibson

(57) ABSTRACT

Described herein are heterogeneous materials comprising a p-type semiconductor comprising two metal oxide compounds of the same metal in two different oxidation states and an n-type semiconductor having a deeper valence band than the p-type semiconductor valence bands, wherein the semiconductor types are in ionic communication with each other. The heterogeneous materials enhance photocatalytic activity.

20 Claims, 18 Drawing Sheets

(51) Int. Cl.
*B01J 23/75* (2006.01)
*A61L 9/18* (2006.01)
*B01D 53/00* (2006.01)
*B01J 23/02* (2006.01)
*B01J 23/68* (2006.01)
*B01J 27/18* (2006.01)
*B01J 37/04* (2006.01)
*C02F 1/32* (2006.01)
*C02F 1/72* (2006.01)
*C02F 101/32* (2006.01)

(52) U.S. Cl.
CPC .............. *B01J 21/063* (2013.01); *B01J 23/02* (2013.01); *B01J 23/682* (2013.01); *B01J 23/687* (2013.01); *B01J 23/72* (2013.01); *B01J 23/75* (2013.01); *B01J 27/1817* (2013.01); *B01J 35/002* (2013.01); *B01J 37/04* (2013.01); *B01J 37/086* (2013.01); *B01J 37/16* (2013.01); *C02F 1/32* (2013.01); *C02F 1/725* (2013.01); *B01D 2255/802* (2013.01); *C02F 2101/322* (2013.01); *C02F 2305/10* (2013.01)

(56) References Cited

U.S. PATENT DOCUMENTS

| | | | | |
|---|---|---|---|---|
| 5,726,347 | A | * 3/1998 | De Haan | G01N 27/12 338/224 |
| 2002/0057755 | A1 | * 5/2002 | Hemmi | G21C 19/307 376/313 |
| 2003/0150707 | A1 | * 8/2003 | Carmignani | A61L 2/088 204/157.3 |
| 2010/0307593 | A1 | * 12/2010 | Thimsen | B01J 21/063 136/263 |
| 2013/0180932 | A1 | 7/2013 | Fukumura et al. | |
| 2013/0192976 | A1 | 8/2013 | Sambandan et al. | |
| 2014/0158641 | A1 | 6/2014 | Mukherjee et al. | |

OTHER PUBLICATIONS

Johan et al, Annealing Effects on the Properties of Copper Oxide Thin Films Prepared by Chemical Deposition, int. j. eletrco. sci. 6, pp. 6094-6104 (Year: 2011).*
Pelaez, A Review on the Visible Light Active Titanium Dioxide Photocatalysts for Environmental Applications (Year: 2012).*
Ii et al, Photocatalytic activity of WOx—TiO2 under visible light irradiation, journal of photochemistry and photobiology A: chemistry 141, pp. 209-217 (Year: 2001).*
Ke et al, preparation and photocatalytic activity of wo3/tio2 nanocomposite particles, materials letters 62, pp. 447-450 (Year: 2008).*
Munoz-batista et al, Role of Interface Contact in CeO2—TiO2 Photocatalytic Composite Materials, acs catal., 4, 63-72 (Year: 2013).*
International Search Report & Written Opinion of PCT/US2015-049805, dated Dec. 12, 2015.

* cited by examiner

MULTIVALENCE SEMICONDUCTOR PHOTOCATALYTIC MATERIALS

CROSS REFERENCE TO RELATED APPLICATIONS

This application is a national phase of PCT/US2015/049805 filed on Sep. 11, 2016 which claims priority to U.S. 62/050,030 filed on Sep. 12, 2014, the entire disclosures of which are incorporated by reference.

FIELD OF THE DISCLOSURE

The current disclosure describes heterogeneous materials which are useful in photocatalytic materials.

BACKGROUND OF THE DISCLOSURE

Visible light activated photocatalysts can be deployed for self-cleaning, air and water purification and many other interesting applications usually without any post-deployment, non-renewable energy costs. This is because the photocatalysts are able to decompose pollutants (like dyes, volatile organic compounds and $NO_x$) using ambient light like solar radiation or indoor and outdoor lighting. With the anticipated rapid adoption of UV-free indoor lighting (like LEDs and OLEDs), it would be helpful to find ways to deploy visible-light activated photocatalysts in indoor applications, for instance, in cleaning room air in domestic, public and commercial spaces, especially in confined areas like aircraft, public buildings, etc. Moreover, additional applications for antibacterial surfaces and self-cleaning materials can have wide applicability in the food service, transportation, health care, and hospitality sectors.

Elemental copper, copper composites, alone or in combination with metal oxides, may be useful as photocatalytic/antibacterial/antiviral materials. Elemental copper, however, shows a degradation of antibacterial activity over time (durability) and unappealing cosmetic appearance change (from copper (Cu) metal to black copper oxide (CuO)), both believed due to oxidation of elemental copper under normal application conditions. Thus, there is a need for improved longevity of antibacterial activity over time. Thus, there is a need for photocatalytic materials that provide antibacterial/antiviral activity without unappealing cosmetic appearance changes.

The current disclosure describes heterogeneous materials having a p-type semiconductor comprising mixed valence oxide compounds and an n-type semiconductor having a deeper valence band than that of the p-type semiconductor, wherein the semiconductors are in ionic charge communication with each other. These multivalent heterogeneous materials can be used to enhance the photocatalytic activity of photocatalytic materials and to improve durability (i.e., maintain photocatalytic activity over time). Photocatalytic materials are useful for having and/or enhancing antibacterial (light and dark) activity, antiviral activity, decomposition of volatile organic compounds (VOC), and/or dye discoloration in aqueous solutions.

SUMMARY OF THE DISCLOSURE

Some embodiments include a heterogeneous material comprising: a p-type semiconductor comprising a first metal oxide compound and a second metal oxide compound, wherein the first metal oxide compound and the second metal oxide compound have different oxidation states of the same metal, and wherein the p-type semiconductor has a p-type valence band; a first n-type semiconductor having an n-type valence band which is deeper than the p-type valence band, wherein the first n-type semiconductor is in ionic charge communication with the p-type semiconductor; and a second n-type semiconductor.

In some embodiments, the n-type semiconductor is 90 to 99.999 wt % of the heterogeneous material.

The n-type semiconductor can be any suitable semiconductor wherein the charge carriers are electrons, such as electrons in the conduction band which are donated from a donor band of a dopant. In another embodiment, the n-type semiconductor is an oxide comprising cerium, tungsten, tantalum, tin, zinc, strontium, zirconium, barium, indium, or aluminum oxide. In another embodiment, the n-type semiconductor is $Sn-Ti(O,C,N)_2$, $CeO_2$, $KTaO_3$, $Ta_2O_5$, $SnO_2$, $WO_3$, $ZnO$, $SrTiO_3$, $BaTiO_3$, $ZrTiO_4$, $In_2TiO_5$, $Al_2TiO_5$, or $LiCa_2Zn_2V_3O_{12}$. In another embodiment, the n-type semiconductor is $Sn-Ti(O,C,N)_2$. In another embodiment, the n-type semiconductor is $Al_{2-x}In_xTiO_5$ wherein $0<x<2$. In another embodiment, the n-type semiconductor is $Zr_{1-y}Ce_y TiO_4$ wherein $0<y<1$.

In another embodiment, the n-type semiconductor can comprise an oxide comprising titanium. In another embodiment, the oxide comprising titanium further comprises a plural phase titanium oxide. In another embodiment, the plural phase titanium oxide comprises a mixture of anatase $TiO_2$ phase and rutile $TiO_2$ phase.

In another embodiment, the n-type semiconductor is a titanium oxide having a dopant. For example, a dopant could donate electrons to the conducting band of titanium oxide. In another embodiment, the n-type semiconductor is a titanium oxide doped with N, C, or both. In another embodiment, the n-type semiconductor is a titanium oxide comprising a compound represented by the formula $(Ti_{1-r}M_r)(O_{2-s-t}C_sN_t)$, wherein: M is Sn, Ni, Sr, Ba, Fe, Bi, V, Mo, W, Zn, Cu, or combinations thereof; r is in the range of 0 to 0.25; s is in the range of 0.001 to 0.1; and t is in the range of 0.001 to 0.1.

Another embodiment comprises a photocatalyst $(Ti_{0.99}Sn_{0.01})(O_{2-s-t}C_sN_t)$, $(Ti_{0.97}Sn_{0.03})(O_{2-s-t}C_sN_t)$, $(Ti_{0.95}Sn_{0.05})(O_{2-s-t}C_sN_t)$, $(Ti_{0.90}Sn_{0.10})(O_{2-s-t}C_sN_t)$, $(Ti_{0.85}Sn_{0.15})(O_{2-s-t}C_sN_t)$, $(Ti_{0.985}Ni_{0.015})(O_{2-s-t}C_sN_t)$, $(Ti_{0.98}Ni_{0.02})(O_{2-s-t}C_sN_t)$, $(Ti_{0.97}Ni_{0.03})(O_{2-s-t}C_sN_t)$, $(Ti_{0.99}Sr_{0.01})(O_{2-s-t}C_sN_t)$, $(Ti_{0.97}Sr_{0.03})(O_{2-s-t}C_sN_t)$, $(Ti_{0.95}Sr_{0.05})(O_{2-s-t}C_sN_t)$, $(Ti_{0.97}V_{0.03})(O_{2-s-t}C_sN_t)$, $(Ti_{0.95}Ba_{0.05})(O_{2-s-t}C_sN_t)$, $(Ti_{0.94}Sn_{0.05}Fe_{0.01})(O_{2-s-t}C_sN_t)$, $(Ti_{0.94}Sn_{0.05}Ni_{0.01})(O_{2-s-t}C_sN_t)$, $(Ti_{0.99}Fe_{0.01})(O_{2-s-t}C_sN_t)$, $(Ti_{0.95}Zn_{0.05})(O_{2-s-t}C_sN_t)$, $(Ti_{0.775}n_{0.15}Cu_{0.08})(O_{2-s-t}C_sN_t)$, $(Ti_{0.85}Zn_{0.15})(O_{2-s-t}C_sN_t)$, $(Ti_{0.90}Bi_{0.10})(O_{2-s-t}C_sN_t)$, $(Ti_{0.996}V_{0.004})(O_{2-s-t}C_sN_t)$, $(Ti_{0.984}V_{0.016})(O_{2-s-t}C_sN_t)$, $(Ti_{0.97}V_{0.03})(O_{2-s-t}C_sN_t)$, $(Ti_{0.997}Mo_{0.003})(O_{2-s-t}C_sN_t)$, $(Ti_{0.984}Mo_{0.016})(O_{2-s-t}C_sN_t)$, $(Ti_{0.957}Mo_{0.043})(O_{2-s-t}C_sN_t)$, $(Ti_{0.97}W_{0.03})(O_{2-s-t}C_sN_t)$, $(Ti_{0.95}W_{0.05})(O_{2-s-t}C_sN_t)$, $(Ti_{0.996}V_{0.004})(O_{2-s-t}C_sN_t)$, $(Ti_{0.984}V_{0.016})(O_{2-s-t}C_sN_t)$, or $(Ti_{0.97}V_{0.03})(O_{2-s-t}C_sN_t)$.

Some embodiments include a method of decomposing a chemical compound comprising exposing the chemical compound to a photocatalyst comprising a homogeneous material described herein in the presence of light. In some embodiments, the chemical compound is a pollutant, such as a volatile organic compound.

Some embodiments include a method of killing a microbe comprising exposing the microbe to a photocatalyst comprising a homogeneous material described herein in the presence of light.

Some embodiments include a method of preparing a heterogeneous material comprising: heating a mixture of 1)

a first n-type semiconductor and a second n-type semiconductor; and 2) an aqueous solution comprising a copper ion complex; wherein the first n-type semiconductor and the second n-type semiconductor are mixed together and then combining the first and second n-type semiconductor mixture with the aqueous solution comprising the copper ion complex.

A particular embodiment as described herein includes a method for loading a mixed valence compound. This method can include adding a dispersing agent to a mixed valence-type compound to more positively charge the surface of the n-type compound; adding an attracting agent to the n-type compounds to make the surface charge of the n-type semiconductor more negative; and mixing the dissimilarly charged materials with each other at a temperature below the doping temperature of the mixed valence compound.

DETAILED DESCRIPTION

The current disclosure describes heterogeneous materials having a p-type semiconductor comprising a mixed valence oxide compound. The p-type semiconductor has a p-type valence band. The heterogeneous material also comprises an n-type semiconductor having an n-type valence band which is deeper valence band than the p-type valence band. In the heterogeneous material, the n-type semiconductor is in ionic charge communication with the mixed valence oxide compound. These multivalent heterogeneous materials can be used to enhance the photocatalytic activity of photocatalytic materials and to improve durability (i.e., maintain photocatalytic activity over time). Photocatalytic materials are useful for having and/or enhancing antibacterial (light and dark) activity, antiviral activity, decomposition of volatile organic compounds (VOC), and/or dye discoloration in aqueous solutions.

A heterogeneous material can be any material having more than 1 solid phase or solid material, including physical mixtures of particles homogeneous or heterogeneous particles having different compositions and/or composite particles, and containing a p-type semiconductor comprising a first metal oxide compound and a second metal oxide compound having different oxidation states of the same metal, a first n-type semiconductor, and a second n-type semiconductor. The material made be in the form of particles, wherein each particle contains the p-type semiconductor, the first n-type semiconductor, and the second n-type semiconductor in 2, 3 or more different solid phases. Alternatively, some particles may have some, but not all of the p-type semiconductor, the first n-type semiconductor, and the second n-type semiconductor. In some embodiments, the heterogeneous material is in the form of a powder.

A heterogeneous material can be composed of particles having a particle size, such as an average particle size, of less than 200 nm; less than 190 nm; less than 180 nm; less than 170 nm; less than 160 nm; less than 150 nm; less than 140 nm; less than 130 nm; less than 120 nm; less than 110 nm; less than 100 nm; less than 90 nm; less than 80 nm; less than 70 nm; less than 60 nm; less than 50 nm; less than 40 nm; less than 30 nm; less than 20 nm; or less than 10 nm. In a particular embodiment, the particle size of the mixed valence compounds is 100 nm or less.

Figure 1C:
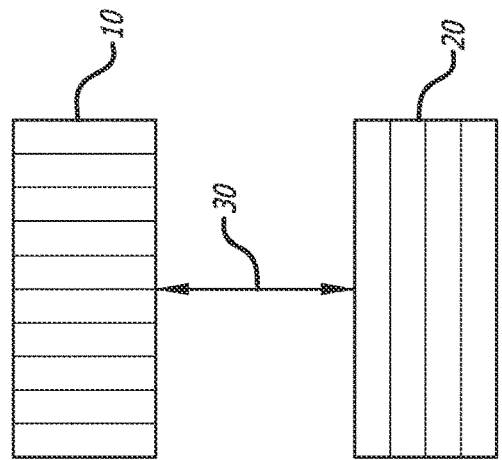
FIG. 1C is a schematic showing the relationship between conduction energy bands with valence energy bands for non-conducting materials.
Figure 1B:
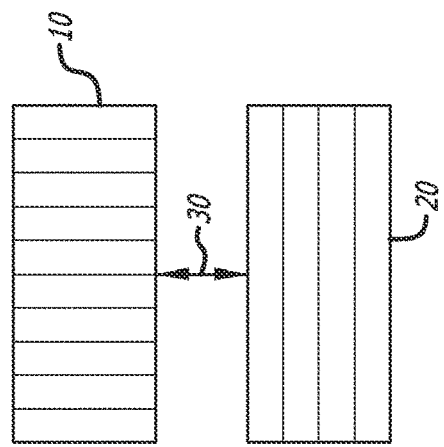
FIG. 1B is a schematic showing the relationship between conduction energy bands with valence energy bands for semi-conductor materials.
Figure 1A:
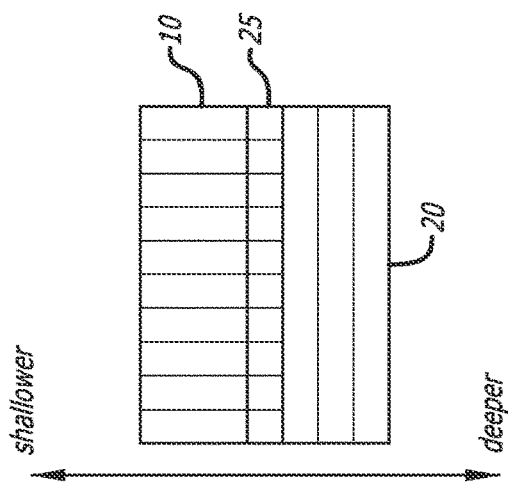
FIG. 1A is a schematic showing the relationship between conduction energy bands with valence energy bands for metal materials.

As shown in FIGS. 1A-C, a conduction band 10 is a range of electron energies low enough to allow an electron to be freed from binding with its atom to move freely within the atomic lattice of the material as a delocalized electron. In semiconductors, the valence band 20 is the highest range of electron energies in which electrons are normally present at absolute zero temperature. The valence electrons are substantially bound to individual atoms, as opposed to conduction electrons (found in semiconductors), which can move more freely within the atomic lattice of the material. On a graph of the electronic band structure of a material, the valence band 20 is generally located below the conduction band, separated from it in insulators and semiconductors by a band gap 30. In some materials, the conduction band has substantially no discernible energy gap separating it from the valence band. The conduction and valence bands may actually overlap (overlap 25), for example, when the valence band level energy is higher or less negative than the conduction band level energy.

Various materials may be classified by their band gap; e.g., classified by the difference between the valence band 20 and conduction band 10. In non-conductors (e.g., insulators), the conduction band is much higher energy than the valence band, so it takes much too much energy to displace the valence electrons for an insulator to effectively conduct electricity. These insulators are said to have a non-zero band gap. In conductors, such as metals, that have many free electrons under normal circumstances, the conduction band 10 overlaps with the valence band 20—there is no band gap, so it takes very little or no additional applied energy, to displace the valence electrons. In semiconductors, the band gap is small, on the order of 200 nm to 1000 nm. While not intending to be bound by theory, this is believed to be the reason that it takes relatively little energy (in the form of heat or light) to make semiconductors' electrons move from the valence band to another energy level and conduct electricity; hence, the name semiconductor.

In some embodiments, an heterogeneous material is provided that comprises a p-type semiconductor comprising a mixed valence oxide compound, the compound having a p-type conduction band and a p-type valence band; and a separate n-type semiconductor having an n-type valence band that is deeper, lower energy, or more negative than the p-type valence band.

A heterogeneous material may comprise any suitable p-type semiconductor, including any semiconductor wherein the charge carrier is effectively positive holes. These holes may be present in a p-type valence band, which can be essentially full of electrons, except for a few holes which may essentially carry the positive charge. In some embodiments, a p-type semiconductor may comprise a combination of a first metal oxide compound and a second metal oxide compound, which may have different oxidation states of the same metal, e.g. Cu(I) and Cu(II); Co(II) and Co(III); Mn(II) and Mn(III); Fe(II) and Fe(III); Ir(III) and Ir(IV); and combinations thereof. In particular embodiments, copper(I) and copper(II) compounds can be $Cu_xO$ compounds, or may include $Cu^{1+}$ and $Cu^{2+}$. Ratios of mixed valence oxide compounds can be 10% to 90%: 90% to 10% (metal of lower oxidation state:metal of higher oxidation state). Particular ratios can also include: 15% to 85%; 20% to 80%; 25% to 75%; 30% to 70%; 35% to 65%; 40% to 60%; 45% to 55%; 50% to 50%; 55% to 45%; 60% to 40%; 65% to 35%; 70% to 30%; 75% to 25%; 80% to 20%; and 85% to 15% (metal of lower oxidation state:metal of higher oxidation state).

For mixed valence metal oxide compounds that include $Cu^{1+}$ and $Cu^{2+}$, in some embodiments $Cu^{1+}:Cu^{2+}$ may have a ratio of about 10%:90% to about 90%:10%, about 10%: 90% to about 30%:70%; about 15%:85% to about 25%: 75%, about 15%:85%; about 20%:80%; about 25%:75%; about 30%:70%; about 35%:65%; about 40%:60%; about 45%:55%; about 50%:50%; about 55%:45%; about 60%: 40%; about 65%:35%; about 70%:30%; about 75%:25%; about 80%:20%; or about 85%:15%. In some embodiments the ratios are $Cu^{1+}:Cu^{2+}$ wt %. In some embodiments the ratios are $Cu^{1+}:Cu^{2+}$ molar %.

In some embodiments, wherein the n-type semiconductor in ionic charge communication with the p-type semiconductor, the p-type semiconductor is loaded onto the n-type semiconductor. In some embodiments, wherein the n-type semiconductor in ionic charge communication with the p-type semiconductor, the p-type semiconductor can be embedded, layered, in contact with and/or deposited onto the n-type semiconductor. In some embodiments, the p-type semiconductor mixed valence compounds are substantially uniformly dispersed onto the first n-type semiconductor. The particle size of the mixed valence compounds can be less than 200 nm; less than 190 nm; less than 180 nm; less than 170 nm; less than 160 nm; less than 150 nm; less than 140 nm; less than 130 nm; less than 120 nm; less than 110 nm; less than 100 nm; less than 90 nm; less than 80 nm; less than 70 nm; less than 60 nm; less than 50 nm; less than 40 nm; less than 30 nm; less than 20 nm; or less than 10 nm. In a particular embodiment, the particle size of the mixed valence compounds is 100 nm or less.

In some embodiments, the p-type semiconductor comprises from 0.001 to 10 wt % of the heterogeneous material and the first n-type semiconductor comprises from 99.999 to 90 wt % of the heterogeneous material. In additional embodiments, the p-type semiconductor comprises 0.001 wt %, 0.005 wt %, 0.01 wt %, 0.05 wt %, 0.1 wt %, 0.5 wt %, 1 wt %, 2 wt %, 3 wt %, 4 wt %, 5 wt %, 6 wt %, 7 wt %, 8 wt %, 9 wt %, or 10 wt % of the heterogeneous material. In additional embodiments, the first n-type semiconductor comprises 90 wt %, 91 wt %, 92 wt %, 93 wt %, 94 wt %, 95 wt %, 96 wt %, 97 wt %, 98 wt %, 99 wt %, 99.1 wt %, 99.2 wt %, 99.3 wt %, 99.4 wt %, 99.5 wt %, 99.6 wt %, 99.7 wt %, 99.8 wt %, or 99.5 wt % of the heterogeneous material.

In another embodiment, the p-type semiconductor comprises a mixed valence oxide compound comprising a pair of the same metallic chemical element, e.g. copper (Cu), cobalt (Co), manganese (Mn), iron (Fe), iridium (Ir), etc., in two different oxidation states, such as the pairs Cu(I) and Cu(II); Co(II) and Co(III); Mn(II) and Mn(III); Fe(II) and Fe(III); and Ir(III) and Ir(IV).

In another embodiment, the p-type semiconductor is loaded onto the n-type semiconductor. In another embodiment, the p-type semiconductors are substantially uniformly dispersed onto the n-type semiconductor.

In another embodiment, the mixed valence oxide compounds have a particle size of 100 nm or less.

In some embodiments, the p-type semiconductor comprises $Cu_xO$, such as $Cu_xO$ comprising two different oxidation states of copper, e.g. Cu(I) and Cu(II). In another embodiment, the $Cu_xO$ compound is chemically valence controlled. In another embodiment, the ratio of Cu(I):Cu(II) is between 10:90 to 90:10.

In some embodiments, the p-type semiconductor comprises a mixture of copper oxides, such as a first copper oxide compound and a second copper oxide, such as a Cu(I) compound (e.g. $Cu_2O$) and a Cu(II) compound (e.g. CuO). In some embodiments, the p-type semiconductor comprises Cu(I) (e.g. $Cu_2O$) and Cu(II) (e.g. CuO) in a weight:weight or a mole:mole ratio [Cu(I):Cu(II)] of about 1:9 to about 3:7, about 1:3 to about 1:6, or about 1:3 to about 1:4.

In some embodiments, a p-type semiconductor, such as $Cu_xO$, is about 0.001 wt % to about 10 wt %, about 0.001 wt % to about 5 wt %, about 0.01 wt % to about 1 wt %, about 0.05 wt % to about 0.5 wt %, about 0.01 wt %, about 0.05 wt %, about 0.5 wt % of the heterogeneous material, or any amount in a range bounded by, or between, any of these values.

Some embodiments include a p-type semiconductor of the previous paragraph in combination with a first n-type semiconductor that is a titanium oxide or $Ti(O,C,N)_2$ doped with tin, or a titanium oxide, such as $TiO_2$, having more than one phase. In some embodiments, such a $TiO_2$ can have two phases, such as rutile $TiO_2$ and anatase $TiO_2$. In some embodiments, the n-type semiconductor can be about 70% to about 90% anatase phase and 10% to about 30% rutile phase $TiO_2$, about 80% to about 90% anatase phase and 10% to about 20% rutile phase $TiO_2$, about 75% to about 80% anatase phase and 20% to about 25% rutile phase $TiO_2$, or about 83% anatase phase $TiO_2$ and 17% rutile phase $TiO_2$. Some embodiments include a p-type semiconductor of the previous paragraph in combination with an first n-type semiconductor that is tin oxide. In some embodiments, the first n-type semiconductor comprises $WO_3$.

With respect to a semiconductor comprising a p-type semiconductor having a mixture of copper oxides and an n-type semiconductor that is a titanium oxide or $Ti(O,C,N)_2$ doped with tin, or a titanium oxide, such as $TiO_2$, having more than one phase, in some embodiments, the copper oxides may be about 0.1% to about 5%, about 0.2% to about 2%, about 0.2% to about 1.5%, about 0.5%, or about 1% of the total weight of the n- and p-type semiconductors.

Figure 2:
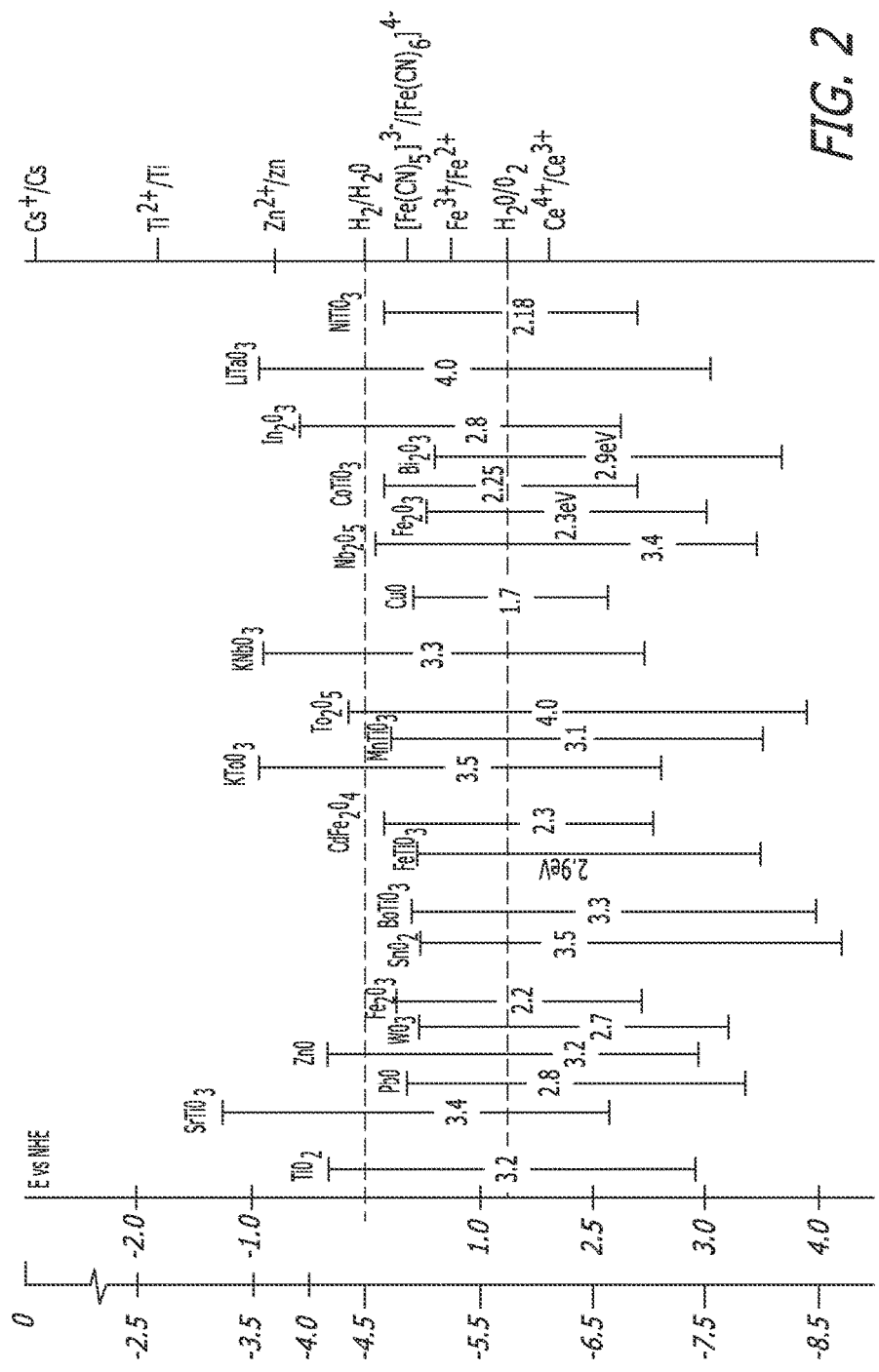
FIG. 2 is a schematic showing the conduction and valence energy band levels for various compounds described herein.

The first n-type semiconductor should be in ionic charge communication with the p-type semiconductor, meaning that ionic charge can be transferred from the n-type semiconductor to the mixed valence oxide compound or from the mixed valence oxide compound to the n-type semiconductor. Examples of suitable conduction bands and valence bands are shown in FIG. 2. While not intending to be bound by theory, if the valence band of the n-type semiconductor is deeper or more negative than the valence band of the p-type, electrons are more easily able to pass from the n-type to the p-type compound. If the materials are in ionic communication, electrons can pass from one compound to the next, enabling regeneration of the higher valence compound to the lower valence compound. For example, $Cu^{2+}$ can be recycled to $Cu^{1+}$ via this mechanism. In some embodiments, the materials in ionic communication are loaded onto one another. By loading, the materials retain their separate identity; e.g., $Cu_xO$ (p-type semiconductor) separate from $TiO_2$, $Ti(OCN)_2$:Sn, etc. (n-type semiconductor). In particular embodiments, one material is on the surface, in contact with or in close proximity to the other, as opposed to doping, physically separated from the other, ionic charge isolated or admixing (physical mixing). In some embodiments, such contact and/or isolation can be determined by transmission electron microscopy (TEM) examination of the p-type and n-type materials. In other embodiments, the heterogeneous materials are integrated within a compound matrix; e.g., incorporated into the compound/crystal lattice.

In some embodiments, the p-type semiconductor, such as $Cu_xO$, is loaded onto the first n-type semiconductor, such as a combination of anatase $TiO_2$ and rutile $TiO_2$ or $WO_3$. In some embodiments, the n-type semiconductor is an oxide comprising an element that can be cerium, tungsten, tantalum, tin, zinc, strontium, zirconium, barium, indium, or aluminum oxide having a valence band deeper than that of the p-type semiconductor pair valence bands. In some embodiments, the n-type semiconductor can be anatase, rutile, wurtzite, spinel, perovskite, pyrochlore, garnet, zircon and/or tialite phase material or mixtures thereof. Each of these options is given its ordinary meaning as understood by one having ordinary skill in the semiconductor art. Comparison of an x-ray diffraction pattern of a given standard and the produced sample is one of a number of methods that may be used to determine whether the sample comprises a particular phase. Exemplary standards include those XRD spectra provided by the National Institute of Standards and Technology (NIST) (Gaitherburg, Md., USA) and/or the International Centre for Diffraction Data (ICDD, formerly the Joint Committee on Powder Diffraction Standards [JCPDS]) (Newtown Square, Pa., USA). In some embodiments, the perovskite can be a perovskite oxide. In some embodiments, the perovskite oxide can comprise $FeTiO_3$, $YFeO_3$, $LuRhO_3$, $BaSnO_3$, $Ba_{0.8}Ca_{0.2}TiO_3$, $CdSnO_3$, $LaRhO_3$, $LaRhO_3$, $LaMnO_3$, $CoTiO_3$, $CuTiO_3$, $MgTiO_3$, $ZnTiO_3$, $BiNb_{1-x}Ta_xO_4$, where x=0 to 1.00, or $InNb_{1-x}Ta_xO_4$, where x=0 to 1.00.

In additional embodiments, the n-type semiconductor can comprise cerium, tungsten, tantalum, tin, zinc, strontium, zirconium, barium, indium, niobium, vanadium, iron, cadmium, germanium, and/or aluminum oxide. The n-type semiconductor can also comprise $CeO_2$; $MgTa_2O_6$; $BaTa_2O_6$; $SrTa_2O_6$; $Ta_2O_5$; $FeTa_2O_6$; $Hg_2Ta_2O_7$; $Hg_2Nb_2O_7$; $Hg_2Ta_xNb_{1-x}O_7$; $K_3Ta_3Si_2O_{13}$; $K_2LnTa_5O_{15}$; $WO_3$; $ZnO$; $SrTiO_3$; $SrNb_2O_7$; $SrTa_2O_7$; $SrTaNbO_7$; $Sr_2FeNbO_6$; $Sr_3FeNb_2O_9$; $TiO_2$; $SnO_2$; $BaTiO_3$; $FeTiO_3$; $CdFe_2O_4$; $MnTiO_3$; $Cs_2Nb_4O_{11}$; $KNbO_3$; $Sr_2FeNbO_6$; $Sr_3FeNb_2O_9$; $NiNb_2O_6$; $CoNb_2O_6$; $ZnNb_2O_6$; $Nb_2O_5$; $K_4Nb_6O_{17}$; $Rb_4Nb_6O_{17}$; $CuTiO_3$; $BiO_3$; $In_2O_3$; $LiTaO_3$; $NiTiO_3$; $In_2TiO_5$; $Al_2TiO_5$; $Al_{2-x}In_xTiO_5$; $ZrTiO_4$; $Zr_{1-y}Ce_y$-$TiO_4$; $LiCa_2Zn_2V_3O_{12}$; $Cd_2Sna_4$; $CdIn_2O_4$; $Cd_2GeO_4$; $Bi_2W_2O_9$; $Bi_2WO_6$; $Bi_3TiNbO_9$; $ACrO_4$, wherein A can be Sr, Ba or combination of them; $CuMnO_2$; $PbWO_4$; $CuFeO_2$; $InVO_4$; $MVWO_6$, wherein M can be Li, Ag or combination of them; $Bi_2MNbO_7$, wherein M can be Al, Ga, In, Y, rare earth, Fe or combination of them; $Zr_2WO_6$; $PbWO_4$; $SnWO_4$; $Bi_2W_2O_9$; $Na_2W_4O_{13}$; and/or, $MWO_4$, wherein M can be Ca, Zn, Cu or combination of them.

In some embodiments, the n-type semiconductor can be a vanadium garnet semiconducting photocatalyst. In some embodiments, the vanadium garnet semiconducting photocatalyst can be represented by the formula: $(A_{1-x}O_x)_3(M)_2(V_3)O_{12}$, wherein $0<x<1$. In some embodiments, the cumulative ionic charge of $(A_{1-x}O_x)_3$ and $(M)_2$ is +9. In some embodiments, $A^+$ can be $Li^+$, $Cu^+$, $Na^+$, $K^+$, $Ti^+$, $Cd^{2+}$, $Ca^{2+}$, $Sr^{2+}$, $Pb^{2+}$, $Y^{3+}$, $Bi^{3+}$, $Ln^{3+}$, or combinations thereof. In some embodiments, M can be one or an of $Li^+$, $Ni^{2+}$, $Mg^{2+}$, $Co^{2+}$, $Cu^{2+}$, $Zn^{2+}$, $Mn^{2+}$, $Cd^{2+}$, $Cr^{3+}$, $Fe^{3+}$, or $Sc^{3+}$ or combinations thereof.

In some embodiments, the n-type semiconductor can be a vanadium garnet semiconducting photocatalyst. In some embodiments, the vanadium garnet semiconducting photocatalyst can be represented by Formula 1: $(A^{2+})_3(M^+M^{2+})(V_3)O_{12}$. In some embodiments, the vanadium garnet semiconducting photocatalyst can be $Ca_3LiZnV_3O_{12}$ and/or $Sr_3LiZnV_3O_{12}$.

In some embodiments, the first n-type semiconductor can be a mixed titanate. The term "mixed titanate" refers to a compound that comprises Ti, O and at least another element; e.g., Ca, Cu, Mg, or La. In some embodiments, the mixed titanate can be $CaCu_2Ti_3O_{12}$ (perovskite titanate); $MgTi_2O_5$ (pseudobrookite); and/or $La_2Ti_2O_7$ (pyrochlore titanate). In some embodiments, the Ti oxide can comprise a mixture of anatase and rutile $TiO_2$.

In some embodiments, the n-type semiconductor can comprise a mixed copper oxide. Mixed copper oxide refers to an n-type semiconductor comprising Cu, O and another element different from copper and oxygen. In some embodiments, the mixed copper oxide can be $CuMnO_2$ or $CuFeO_2$.

In some embodiments, the n-type semiconductor can be a simple or mixed ferrite. In some embodiments, the mixed ferrite can be Alpha-$Fe_2O_3$; $MFe_2O4$, where M is Mg, Zn, Ca, Ba or combination of them; $Ca_2Fe_2O_5$, $MFe_{12}O_{19}$, where M is Sr, Ba or combination of them; $Sr_7Fe_{10}O_{22}$, $MFeO_{2.5+x}$, where M is Sr, Ba or combination of them, $Sr_3Fe_2O_{6.16}$; $Bi_{1.5}Pb_{0.5}Sr_2BiFe_2O_{9.25}$; $Pb_2Sr_2BiFe_2O_{9+y}$; $Bi_2Sr_2BiFe_2O_{9+y}$; and/or $Bi_{1.5}Pb_{0.5}Sr_4Fe_2O_{10.04}$.

In some embodiments the n-type semiconductor can be a $Cu_xO$ loaded oxynitride semiconducting photocatalyst. In some embodiments the oxynitride semiconducting photocatalyst can comprise TaON; $MTaO_2N$, wherein M is Ca, Sr, Ba, or combination of them; $SrNb_2O_{7-x}N_x$; $(Ga_{1-x}Zn_x)(N_{1-x}O_x)$; and/or $(Zn_{1+x}Ge)(N_2O_x)$.

In some embodiments the n-type semiconductor can be a $Cu_xO$ loaded sulfide, selenide or sulfoselenide semiconducting photocatalyst. In some embodiments, the sulfide, selenide or sulfoselenide semiconducting photocatalyst can comprise $Cd(S_y,Se_{1-y})$, wherein $0<y<1$; $(Cd,Zn(S_y,Se_{1-y})$, wherein $0<y<1$; $(AgIn)_xZn_{2(1-x)}(S_y,Se_{1-y})_2$, wherein $0<y<1$; $(CuIn)_xZn_{2(1-x)}(S_y,Se_{1-y})_2$, wherein $0<y<1$; $(CuAgIn)_xSn_{2(1-x)}(S_y,Se_{1-y})_2$, wherein $0<y<1$; and/or $Sm_2Ti_2S_2O_5$.

In particular embodiments, the n-type semiconductor comprises a compound represented by the formula $Al_{2-x}In_xTiO_5$, wherein x is in the range of 0 to 2 ($0<x<2$). In other particular embodiments, the n-type semiconductor comprises a compound represented by the formula $Zr_{1-y}Ce_yTiO_4$, wherein y is in the range of 0 to 1 ($0<y<1$). In particular embodiments, the n-type semiconductor is a titanium oxide having a valence band controlled through doping. In some embodiments, the n-type semiconductor is a titanium oxide doped with N, C or both. In some embodiments, the titanium oxide comprises a compound represented by the formula $(Ti_{1-r}M_r)(O_{2-s-t}C_sN_t)$, wherein M is Sn, Ni, Sr, Ba, Fe, Bi, V, Mo, W, Zn, Cu, or combinations thereof; r is in the range of 0 to 0.25; s is in the range of 0.001 to 0.1; and, t is in the range of 0.001 to 0.1. In some embodiments, r is no more than 0.20. In some embodiments, r can more particularly be 0; 0.01; 0.02; 0.03; 0.04; 0.05; 0.06; 0.07; 0.08; 0.09; 0.10; 0.11; 0.12; 0.13; 0.14; 0.15; 0.16; 0.17; 0.18; 0.19; 0.20; 0.21; 0.22; 0.23; 0.24; or 0.25. In some embodiments, s can more particularly be 0.001; 0.005; 0.01; 0.02; 0.03; 0.04; 0.05; 0.06; 0.07; 0.08; 0.09; or 0.1. In some embodiments, t can more particularly be 0.001; 0.005; 0.01; 0.02; 0.03; 0.04; 0.05; 0.06; 0.07; 0.08; 0.09; or 0.1.

The materials are also described in co-pending and co-assigned application Ser. No. 13/741,191, filed Jan. 14, 2013, which is incorporated by reference in its entirety for its description of photocatalytic compounds and/or compositions. In some embodiments, M is Sn, Ni, Sr, Ba, Fe, Bi, or combinations thereof. In some embodiments, r is in the range of 0.0001 to 0.15. In some embodiments, M is Sn. In some embodiments, r is at least 0.001. In some embodiments, the n-type semiconductor comprises $(Ti_{0.99}Sn_{0.01})(O_{2-s-t}C_sN_t)$, $(Ti_{0.97}5n_{0.03})(O_{2-s-t}C_sN_t)$, $(Ti_{0.95}Sn_{0.05})(O_{2-s-t}C_sN_t)$, $(Ti_{0.90}Sn_{0.10})(O_{2-s-t}C_sN_t)$, $(Ti_{0.85}Sn_{0.15})(O_{2-s-t}C_sN_t)$, $(Ti_{0.985}Ni_{0.015})(O_{2-s-t}C_sN_t)$, $(Ti_{0.98}Ni_{0.02})(O_{2-s-t}C_sN_t)$, $(Ti_{0.97}Ni_{0.03})(O_{2-s-t}C_sN_t)$, $(Ti_{0.99}Sr_{0.01})(O_{2-s-t}C_sN_t)$, $(Ti_{0.97}Sr_{0.03})(O_{2-s-t}C_sN_t)$, $(Ti_{0.95}Sr_{0.05})(O_{2-s-t}C_sN_t)$, $(Ti_{0.97}Ba_{0.03})(O_{2-s-t}C_sN_t)$, $(Ti_{0.05}Ba_{0.05})(O_{2-s-t}C_sN_t)$, $(Ti_{0.94}Sn_{0.05}Fe_{0.01})(O_{2-s-t}C_sN_t)$, $(Ti_{0.94}Sn_{0.05}Ni_{0.01})(O_{2-s-t}C_sN_t)$, $(Ti_{0.99}Fe_{0.01})(O_{2-s-t}C_sN_t)$, $(Ti_{0.95}Zn_{0.05})(O_{2-s-t}C_sN_t)$, $(Ti_{0.77}Sn_{0.15}Cu_{0.08})(O_{2-s-t}C_sN_t)$, $(Ti_{0.85}Zn_{0.15})(O_{2-s-t}C_sN_t)$, $(Ti_{0.90}Bi_{0.10})(O_{2-s-t}C_sN_t)$, $(Ti_{0.996}V_{0.004})(O_{2-s-t}C_sN_t)$, $(Ti_{0.984}V_{0.016})(O_{2-s-t}C_sN_t)$, $(Ti_{0.97}V_{0.03})(O_{2-s-t}C_sN_t)$, $(Ti_{0.997}Mo_{0.003})(O_{2-s-t}C_sN_t)$, $(Ti_{0.984}Mo_{0.016})(O_{2-s-t}C_sN_t)$, $(Ti_{0.957}Mo_{0.043})(O_{2-s-t}C_sN_t)$, $(Ti_{0.97}W_{0.03})(O_{2-s-t}C_sN_t)$, and/or $(Ti_{0.95}W_{0.05})(O_{2-s-t}C_sN_t)$. In some embodiments, the n-type semiconductor comprises $(Ti_{0.996}V_{0.004})(O_{2-s-t}C_sN_t)$, $(Ti_{0.984}V_{0.016})(O_{2-s-t}C_sN_t)$, and/or $(Ti_{0.97}V_{0.03})(O_{2-s-t}C_sN_t)$.

In some embodiments, wherein the heterogeneous material comprises a p-type semiconductors loaded onto an n-type semiconductor, the heterogeneous material further comprises a second n-type semiconductor. In some embodiments, at least a portion of the second n-type semiconductor is ionic charge isolated from the p-type semiconductor. In some embodiments, at least a portion of the second n-type semiconductor can be physically separated from the p-type semiconductor, ionic charge isolated, admixed and/or not loaded with the p-type semiconductor. In some embodiments, the second n-type semiconductor can be any of those n-type semiconductors described elsewhere in this application. In another embodiment, the second n-type semiconductor comprises a cerium oxide. In another embodiment, the cerium oxide is $CeO_2$. In another embodiment, the second n-type semiconductor comprises plural phase $TiO_2$. In some embodiments, the second n-type semiconductor can comprise $CeO_2$ and/or plural phase n-type semi-conductor compounds. In some embodiments, the second n-type semiconductor comprise anatases phase and rutile phase compounds, such as titanium oxides. In some embodiments, the anatase phase can be 2.5% to about 97.5%, 5% to about 95%, and/or about 10% to about 90%; and the rutile phase can be 97.5% to about 2.5%, 95% to about 5%, and/or about 90% to about 10%. A non-limiting example of a suitable material includes, but is not limited to a $TiO_2$ mixture sold under the brand name P25™ (83% Anatase phase $TiO_2$+ 17% Rutile phase $TiO_2$) sold by Evonik. In some embodiments, the n-type semiconductor physically mixed with p-type loaded on $WO_3$ can comprise $CeO_2$, $TiO_2$, $SrTiO_3$ and/or $KTaO_3$. In some embodiments, the n-type semiconductor physically mixed with p-type loaded on plural phase n-type semi-conductor compounds (e.g., P25™) can comprise unloaded plural phase n-type semi-conductor compounds (e.g., P25™). In some embodiments, the n-type semiconductor physically mixed with p-type loaded on plural phase n-type semi-conductor compounds can comprise $CeO_2$, $TiO_2$, $SrTiO_3$ and/or $KTaO_3$. In some embodiments, the n-type semiconductor can be inorganic. In some embodiments, the inorganic n-type semiconductor can be an oxide, such as a metal dioxide, including $CeO_2$, $TiO_2$, or the like. In some embodiments, the n-type semiconductor can comprise $SiO_2$, $SnO_2$, $Al_2O_3$, $ZrO_2$, $Fe_2O_3$, $Fe_3O_4$, NiO, $Nb_2O_5$, and/or $CeO_2$.

The p-type semiconductor can be loaded onto the surface of particles of an n-type semiconductor. For example, the p-type semiconductor can be loaded onto the surface of particles of the first n-type semiconductor and/or the particles of the second n-type semiconductor. In some embodiments, at least about 20%, at least about 50%, at least about 70%, or at least about 90% of the p-type semiconductor can be loaded onto the surface of particles of the first n-type semiconductor and the particles of the second n-type semiconductor.

In some embodiments, the n-type semiconductor can be $RE_kE_mO_n$, wherein RE is a rare earth element, E is a chemical element or a combination of chemical elements, O is oxygen, and $1 \le k \le 2$, $2 \le m \le 3$, and $0 \le n \le 3$. In some embodiments, the n-type semiconductor can be $RE_pO_q$ where RE can be a rare earth metal and $1 \le p \le 2$, or can be $1 < p < 2$; and $2 \le q \le 3$ or can be $2 < q < 3$. Examples of suitable rare earth elements include scandium, yttrium, and the lanthanide and actinide series of elements. Lanthanide elements include elements with atomic numbers 57 through 71. Actinide elements include elements with atomic numbers 89 through 103. In some embodiments, the n-type semiconductor can be $Ce_xZr_yO_2$ wherein the y/x ratio=0.001 to 0.999. In some embodiments, the n-type semiconductor can be cerium. In some embodiments, the n-type semiconductor can be $CeO_a$ ($a \le 2$). In some embodiments, the n-type semiconductor can be cerium oxide ($CeO_2$).

In some embodiments, the n-type semiconductor can be a non-oxide. In some embodiments, the non-oxide can be a carbide and/or nitride. In some embodiments, the carbide can be silicon carbide.

Some embodiments include a first n-type semiconductor and a second n-type semiconductor. The first n-type semiconductor can comprise any n-type semiconductor described herein. In some embodiments, the first n-type semiconductor comprises $TiO_2$, such as a combination of anatase and rutile $TiO_2$.

In some embodiments, the molar ratio of the first n-type semiconductor, such as $TiO_2$, including a combination of anatase and rutile $TiO_2$, to the second n-type semiconductor is about 0.5 (e.g. 0.5 moles of the first n-type semiconductor and 1 mole of the second n-type semiconductor) to about 10, about 1, about 2, about 5, or any ratio in a range bounded by or between any of these values.

Some embodiments include a first n-type semiconductor and a second n-type semiconductor. The first n-type semiconductor can comprise any n-type semiconductor described herein. In some embodiments, the first n-type semiconductor comprises $WO_3$.

In some embodiments, the molar ratio of the first n-type semiconductor, such as $WO_3$, to the second n-type semiconductor is about 0.5 (e.g., 0.5 moles of the first n-type semiconductor and 1 mole of the second n-type semiconductor) to about 10, about 1, about 2, about 5, or any ratio in a range bounded by or between any of these values.

For heterogeneous materials comprising a first n-type semiconductor and a second n-type semiconductor, the second n-type semiconductor can comprise any n-type semiconductor described herein. In some embodiments, the second n-type semiconductor is $CeO_2$, $TiO_2$, $GeO_2$, or $ZrO_2$. In some embodiments, the second n-type semiconductor is $CeO_2$. In some embodiments, the second n-type semiconductor is $GeO_2$. In some embodiments, the second n-type semiconductor is $ZrO_2$.

In some embodiments, the mole ratio of physical mixture of the n-type semiconductor (e.g., $CeO_2$) with p-type semiconductor loaded $WO_3$ (e.g., $Cu_xO$—$WO_3$) can be 0-99% n-type semiconductor to 100%-1% p-type semiconductor ($Cu_xO$ loaded $WO_3$). In some embodiments, the mole ratio of physical mixture of the n-type semiconductor (e.g., $CeO_2$) with p-type semiconductor loaded $WO_3$ can be 25% to 75% (and every integer in between) of n-type semiconductor to 75% to 25% (and every integer in between) of p-type semiconductor loaded n-type material (e.g., $WO_3$). In some embodiments, the mole ratio of physical mixture of the n-type semiconductor (e.g., $CeO_2$) with p-type semiconductor loaded $WO_3$ can be 40% to 60% (and every integer in between) of n-type semiconductor to 60% to 40% (and every integer in between) of p-type semiconductor loaded n-type material (e.g., $WO_3$).

In some embodiments, the heterogeneous material can further comprise a noble metal in ionic charge communication with the mixed valence oxide compound. In some embodiments, the noble metal is loaded onto the n-type semiconductor. In some embodiments, the noble metal can be, without limitation, rhodium, ruthenium, palladium, silver, osmium, platinum, and/or gold, or mixtures thereof. In one embodiment, the noble metal is platinum.

In some embodiments, a method for loading a mixed valence compound can be adding a p-type precursor to an attracting agent to make the surface charge of the n-type semiconductor more negative, wherein the p-type precursor comprises a copper cation complex. In some embodiments, a method for loading a mixed valence compound comprises adding an attracting agent to the n-type compounds; and combining the n-type and p-type precursors to each other at a temperature below the doping temperature of the mixed valence compounds. In some embodiments, the method further comprises the step of adding a dispersing agent to an n-type compound to more positively charge the surface of the n-type compound.

In some embodiments, a method for loading a mixed valence compound can be adding a dispersing agent to an n-type compound to more positively charge the surface of the n-type compound; adding a p-type precursor to the dispersing agent and n-type compound, wherein the p-type precursor comprises a copper cation complex; adding an attracting agent to the n-type compounds to make the surface charge of the n-type semiconductor more negative; and combining the dissimilarly charged materials with each other at a temperature below the doping temperature of the mixed valence compounds.

In some embodiments, the dispersing agent can be a strong acid. In some embodiments, the dispersing agent can be 4-7M HCl. In some embodiments, the dispersing agent is 6M HCl.

In some methods, a valence control material is added along with the dissimilarly charged materials to control the mixed valence oxides during the synthesis of the mixed valence oxides. In some embodiments, the valence control material is a mild reducing agent. In some embodiments, the valence control material can be at least one of a sugar, a hydrazide, an amino acid, and/or an amide. In some embodiments, the amide can be urea. In some embodiments, the sugar can be sucrose, fructose, and/or glucose. In some embodiments, the sugar is glucose. In some embodiments, the hydrazide can be carbohydrazide, oxalyl dihydrazide, maleic hydrazide, diformyl hydrazine or tetraformyl trisazine. In some embodiments, the amino acid can be at least one of the proteinogenic or natural amino acids. In some embodiments, the amino acid can be an aliphatic amino acid (e.g., glycine, alanine, valine, leucine, and/or isoleucine). In some embodiments, the amino acid can be a hydroxyl or sulfur containing amino acid (e.g., serine, cysteine, threonine and/or methionine). In some embodiments, the amino acid can be cyclic (e.g., proline). In some embodiments, the amino acid can be aromatic (e.g., phenylalanine, tyrosine, and/or tryptophan). In some embodiments, the amino acid can be basic (e.g., histidine, lysine, and/or arginine). In some embodiments, the amino acid is acidic or amide (e.g., aspartate, glutamate, asparagine, and/or glutamine). In some embodiments the amino acid can be selenocysteine and/or pyrrolysine. In some embodiments the amino acid can be non-proteinogenic. In some embodiments the non-proteinogenic amino acids include those not found in proteins (for example, carnitine and GABA). In some embodiments, the non-proteinogenic amino acids can be those in isolation by standard cellular machinery (for example, hydroxyproline and selenomethionine). In some embodiments, the amino acid is soluble in water. In some embodiments the amino acid is soluble in water at 90° C. In some embodiments the amino acid is substantially entirely dissolved in water at 90° C. The term soluble has the ordinary meaning known to a person of ordinary skill in the art.

In some embodiments, the ratio of the mixed valence oxide compounds, e.g., $Cu^{1+}$ compounds and $Cu^{2+}$ compounds, can be controlled by a method of loading the Cu onto the p-type semiconductor including adding the attracting agents. In some embodiments, the attracting agents that can control the ratio of mixed valence oxide compounds can include a monosaccharide and a base compound. In some embodiments, the monosaccharide can be glucose. In some embodiments, the glucose can be D-glucose and/or L-glucose. In some embodiments, the glucose to NaOH ratio can be 10% to 90% 90% to 10%. Particular ratios can also include: 15% to 85%; 20% to 80%; 25% to 75%; 30% to 70%; 35% to 65%; 40% to 60%; 45% to 55%; 50% to 50%; 55% to 45%; 60% to 40%; 65% to 35%; 70% to 30%; 75% to 25%; 80% to 20%; and 85% to 15%. In some embodiments, the base can be NaOH. The $Cu_xO$ compound is valence controlled chemically.

In some embodiments, the attracting agent can be an agent that provides a sufficient amount of hydroxyl ions to bring the pH of the total solution between pH 8.0 to pH 9.0. In some embodiments, the attracting agent can be a strong base. In some embodiments, the attracting agent is a 4-7M strong base. In some embodiments, the attracting agent is 6M NaOH.

In some embodiments, the p-type precursor can be a substantially sodium free compound. In some embodiments, the substantially sodium-free compound can be a copper cation complex. In some embodiments, the copper cation complex can be Bis(Ethylenediamine) copper(II) (BEDCuII), copper(II) tetraamine chloride, copper(II) tetraamine sulfate, copper(II) tetraamine hydroxide and/or mixtures thereof. In some embodiments, the compound can be Bis(Ethylenediamine) copper(II). The structure of BEDCuII is shown below:

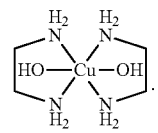

In some embodiments, the doping temperature of the mixed valence compound is between 150° C. to 700° C. In some embodiments, less than the doping temperature of the mixed valence compound is less than 175° C., less than 150° C., less than 125° C. In some embodiments, the mixing temperature is between 75° C. to 125° C. In some embodiments the mixing temperature is 80° C.; 85° C.; 95° C.; 100° C.; 105° C.; 110° C.; 115° C.; 120° C.; or 125° C.

In some embodiments, the precursor selected for the p-type semiconductors can be salts of chloride, acetate, nitrate, sulfate, carbonate, oxide, hydroxide, peroxide, or combinations thereof.

Some heterogeneous materials can be prepared by mixing a first n-type semiconductor, such as $WO_3$, and a second n-type semiconductor, such as $CeO_2$, $TiO_2$, $GeO_2$, or $ZrO_2$, then loading the mixture of n-type semiconductors with a p-type semiconductor, such as $Cu_xO$. For example, a mixture of the first n-type semiconductor and the second n-type semiconductor can be combined with an aqueous solution comprising a precursor of the p-type semiconductor, such as a copper ion complex, and then heated.

Heterogeneous material formed as described above can be isolated by removal of the solvent, for example, by filtering the heterogeneous material out of the solvent.

In some embodiments the described heterogeneous materials have photocatalytic activity. The heterogeneous materials can be antibacterial (light and dark); antiviral; can decompose volatile organic compounds (VOC); and/or can discolor food additive dyes. Suitable non-limiting examples of food additive dyes include natural blue colored powder (Color Maker, Anaheim, Calif., USA) and/or FD&C blue No. 2 synthetic food additive dye (Synthetic blue colored powder, Chromatech, Inc., Michigan, USA). The heterogeneous materials described herein can also increase the durability (time of effectiveness) of photocatalytic materials.

Those of ordinary skill in the art recognize ways to determine whether a heterogeneous material is anti-bacterial (light), e.g., after the heterogeneous material is exposed to visible light. In one embodiment, antibacterial exposure results in at least a reduction of 10% (90% remains), at least 50% (50% remains), at least 99% (at least 1% remains), at least 99.9% (at least 0.1% remains) or at least 100% (0% remains). One example of determining whether the heterogeneous material is anti-bacterial (light) can be by assessing the amount of bacteria present; e.g., a decrease in the amount of bacteria present, after the heterogeneous material is contacted with the bacteria and exposed to visible light. For example, the amount of bacteria present in the sample after exposing the sample for a predetermined time period can be assessed. In some embodiments, the sample can be exposed for 15 minutes, 30 minutes, 1 hour, 2 hours, 5 hours, 7.5 hours, 10 hours, 12 hours, or 24 hours. In some embodiments, the sample is exposed to 800 lux from a fluorescent light source or at least 5 $mW/cm^2$ from a blue LED.

Those of ordinary skill in the art recognize ways to determine whether a heterogeneous material is antibacterial (dark). In one embodiment, antibacterial exposure results in at least a reduction of 10% (at least 90% remains), at least 50% (at least 50% remains), at least 99% (at least 1% remains), at least 99.9% (at least 0.1% remains) or at least 100% (at least 0% remains). One example of determining whether the heterogeneous material is anti-bacterial (dark) can be by assessing the amount of bacteria present, e.g., reduction or decrease in the number of colonies present after the heterogeneous material is contacted with the bacteria without exposure to visible light.

Those of ordinary skill in the art recognize ways to determine whether a heterogeneous material is antiviral. One example of determining whether the heterogeneous material is antiviral can be by assessing, e.g., an inhibition or reduction of the number of virus (phage) colonies. In one embodiment, determining whether the heterogeneous material is antiviral can be by counting the number of viral colonies present over time after exposure to the heterogeneous material. In one embodiment, antiviral exposure results in at least a reduction of 10% (at least 90% remains), at least 50% (at least 50% remains), at least 99% (at least 1% remains), at least 99.9% (at least 0.1% remains) or at least 100% (at least 0% remains).

Those of ordinary skill in the art recognize ways to determine whether a heterogeneous material decomposes volatile organic compounds. One example of determining whether the heterogeneous material decomposes volatile organic compounds can be by assessing the degradation of the organic compound under electromagnetic radiation, for example visible light. In one embodiment, determining acetaldehyde degradation as a decrease or percentage of the initial degradation is an optional way to determine decomposition of volatile organic compounds; e.g., ranging from 0% to 90% over time; or, from 3 to 10 hours or 5 hours under an amount of visible light such as a blue light emitting LED of 455 nm having 270 mW/cm$^2$ power. In some embodiments, the degradation is at least 50%, 60%, 70%, 80%, 90%, or 100% of the initial amount of acetylaldehyde after exposure to the heterogeneous material.

Those of ordinary skill in the art recognize ways to determine whether a heterogeneous material discolors food additives or dyes. One example of determining the discoloration of food additive dyes can be by the decrease or percentage of the initial amount of food dye additive over time. In one example, the food additive can be the natural anthocyanin food additive dye or an FDC food additive dye. In some embodiments, the discoloration of food dye additives can be from 0% to 60% after 5 hours under a blue LED emitting at 455 nm with 45 mW/cm$^2$ power. In some embodiments, the degradation is at least 25%, 30%, 40%, 50%, and/or 60% of the initial amount of the natural anthocyanin food additive dye after exposure to the heterogeneous material.

Those of ordinary skill in the art recognize ways to determine whether a heterogeneous material maintains an activity over time; e.g., the durability of the heterogeneous material. In some embodiments, the discoloration of food dye additives decreased from 0% to 60% after 5 hours under a blue LED emitting at 455 nm with 45 mW/cm$^2$ power. For example, in some embodiments, the retention of antibacterial activity is after exposure to 85% relative humidity and 85° C. for at least 7 days.

Exemplary but non-limiting embodiments are as follows:

Embodiment 1

A heterogeneous material comprising:
a p-type semiconductor comprising a first metal oxide compound and a second metal oxide compound, wherein the first metal oxide compound and the second metal oxide compound have different oxidation states of the same metal, and wherein the p-type semiconductor has a p-type valence band; and an n-type semiconductor having an n-type valence band which is deeper than the p-type valence band, wherein the n-type semiconductor is in ionic charge communication with the p-type semiconductor.

Embodiment 2

The heterogeneous material of embodiment 1, further comprising a noble metal in ionic charge communication with the first metal oxide compound and the second metal oxide compound.

Embodiment 3

The heterogeneous material of embodiment 2, wherein the noble metal is rhodium, ruthenium, palladium, silver, osmium, platinum, or gold.

Embodiment 4

The heterogeneous material of embodiment 2 or 3, wherein the noble metal is loaded onto the n-type semiconductor.

Embodiment 5

The heterogeneous material of embodiment 1, 2, 3, or 4, further comprising a second n-type semiconductor, wherein at least a portion of the second n-type semiconductor is ionic charge isolated from the p-type semiconductor.

Embodiment 6

The heterogeneous material of embodiment 5, wherein the second n-type semiconductor comprises a cerium oxide.

Embodiment 7

The heterogeneous material of embodiment 6, wherein the cerium oxide is $CeO_2$.

Embodiment 8

The heterogeneous material of embodiment 5, wherein the second n-type semiconductor comprises plural phase $TiO_2$.

Embodiment 9

The heterogeneous material of embodiment 1, 2, 3, 4, 5, 6, 7, or 8, wherein the first metal oxide compound comprises Cu(I) and the second metal oxide compound comprises Cu(II), the first metal oxide compound comprises Co(II) and the second metal oxide compound comprises Co(III), the first metal oxide compound comprises Mn(II) and the second metal oxide compound comprises Mn(III), the first metal oxide compound comprises Fe(II) and the second metal oxide compound comprises Fe(III), or, the first metal oxide compound comprises and Ir(III) and the second metal oxide compound comprises Ir(IV).

Embodiment 10

The heterogeneous material of embodiment 1, 2, 3, 4, 5, 6, 7, 8, or 9, wherein the p-type semiconductor is loaded onto the n-type semiconductor.

Embodiment 11

The heterogeneous material of embodiment 1, 2, 3, 4, 5, 6, 7, 8, or 9, wherein the p-type semiconductor is substantially uniformly dispersed onto the n-type semiconductor.

Embodiment 12

The heterogeneous material of embodiment 1, 2, 3, 4, 5, 6, 7, 8, 9, 10, or 11, wherein the p-type semiconductor is in the form of particles having a particle size of 100 nm or less.

Embodiment 13

The heterogeneous material of embodiment 9, wherein the p-type semiconductor comprises Cu(I) and Cu(II).

Embodiment 14

The heterogeneous material of embodiment 13, wherein the p-type semiconductor comprises $Cu_xO$.

Embodiment 15

The heterogeneous material of embodiment 14, wherein the $Cu_xO$ is chemically valence controlled.

Embodiment 16

The heterogeneous material of embodiment 9, wherein the ratio of Cu(I):Cu(II) is between 10:90 to 30:70.

Embodiment 17

The heterogeneous material of embodiment 1, 2, 3, 4, 5, 6, 7, 8, 9, 10, 11, 12, 13, 14, 15, or 16, wherein the p-type semiconductor is 0.001 to 10 wt % of the heterogeneous material and the n-type semiconductor is 90 to 99.999 wt % of the heterogeneous material.

Embodiment 18

The heterogeneous material of embodiment 1, 2, 3, 4, 5, 6, 7, 8, 9, 10, 11, 12, 13, 14, 15, 16, or 17, wherein the n-type semiconductor is an oxide of cerium, tungsten, tantalum, tin, zinc, strontium, zirconium, barium, indium, or aluminum.

Embodiment 19

The heterogeneous material of embodiment 1, 2, 3, 4, 5, 6, 7, 8, 9, 10, 11, 12, 13, 14, 15, 16, or 17, wherein the n-type semiconductor comprises $Sn-Ti(O,C,N)_2$, $MgTi_2O_5$, $CeO_2$, $KTaO_3$, $Ta_2O_5$, $SnO_2$, $WO_3$, $ZnO$, $SrTiO_3$, $BaTiO_3$, $ZrTiO_4$, $In_2TiO_5$, $Al_2TiO_5$, or $LiCa_2Zn_2V_3O_{12}$.

Embodiment 20

The heterogeneous material of embodiment 1, 2, 3, 4, 5, 6, 7, 8, 9, 10, 11, 12, 13, 14, 15, 16, or 17, wherein the n-type semiconductor is $Al_{2-x}In_xTiO_5$ wherein $0<x<2$.

Embodiment 21

The heterogeneous material of embodiment 1, 2, 3, 4, 5, 6, 7, 8, 9, 10, 11, 12, 13, 14, 15, 16, or 17, wherein the n-type semiconductor is $Zr_{1-y}Ce_yTiO_4$ wherein $0<y<1$.

Embodiment 22

The heterogeneous material of embodiment 1, 2, 3, 4, 5, 6, 7, 8, 9, 10, 11, 12, 13, 14, 15, 16, or 17, wherein the n-type semiconductor is a titanium oxide having a valence band controlled through doping.

Embodiment 23

The heterogeneous material of embodiment 1, 2, 3, 4, 5, 6, 7, 8, 9, 10, 11, 12, 13, 14, 15, 16, or 17, wherein the n-type semiconductor is a titanium oxide doped with N, C, or both.

Embodiment 24

The heterogeneous material of embodiment 22, wherein the n-type semiconductor is a titanium oxide comprising a compound represented by the formula $(Ti_{1-r}M_r)(O_{2-s-t}C_sN_t)$, wherein:
  M is Sn, Ni, Sr, Ba, Fe, Bi, V, Mo, W, Zn, Cu, or a combination thereof;
  r is from 0 to 0.25;
  s is from 0.001 to 0.1; and
  t is from 0.001 to 0.1.

Embodiment 25

The heterogeneous material of embodiment 24, comprising $(Ti_{0.99}Sn_{0.01})(O_{2-s-t}C_sN_t)$, $(Ti_{0.97}Sn_{0.03})(O_{2-s-t}C_sN_t)$, $(Ti_{0.95}Sn_{0.05})(O_{2-s-t}C_sN_t)$, $(Ti_{0.90}Sn_{0.10})(O_{2-s-t}C_sN_t)$, $(Ti_{0.85}Sn_{0.15})(O_{2-s-t}C_sN_t)$, $(Ti_{0.985}Ni_{0.015})(O_{2-s-t}C_sN_t)$, $(Ti_{0.98}Ni_{0.02})(O_{2-s-t}C_sN_t)$, $(Ti_{0.97}Ni_{0.03})(O_{2-s-t}C_sN_t)$, $(Ti_{0.99}Sr_{0.01})(O_{2-s-t}CsNt)$, $(Ti_{0.97}Sr_{0.03})(O_{2-s-t}C_sN_t)$, $(Ti_{0.95}Sr_{0.05})(O_{2-s-t}C_sN_t)$, $(Ti_{0.97}Ba_{0.03})(O_{2-s-t}C_sN_t)$, $(Ti_{0.95}Ba_{0.05})(O_{2-s-t}C_sN_t)$, $(Ti_{0.94}Sn_{0.05}Fe_{0.01})(O_{2-s-t}C_sN_t)$, $(Ti_{0.94}Sn_{0.05}Ni_{0.01})(O_{2-s-t}C_sN_t)$, $(Ti_{0.99}Fe_{0.01})(O_{2-s-t}C_sN_t)$, $(Ti_{0.95}Zn_{0.05})(O_{2-s-t}C_sN_t)$, $(Ti_{0.77}Sn_{0.15}Cu_{0.08})(O_{2-s-t}C_sN_t)$, $(Ti_{0.85}Zn_{0.15})(O_{2-s-t}C_sN_t)$, $(Ti_{0.90}Bi_{0.10})(O_{2-s-t}C_sN_t)$, $(Ti_{0.996}V_{0.004})(O_{2-s-t}C_sN_t)$, $(Ti_{0.984}V_{0.016})(O_{2-s-t}C_sN_t)$, $(Ti_{0.97}V_{0.03})(O_{2-s-t}C_sN_t)$, $(Ti_{0.997}Mo_{0.003})(O_{2-s-t}C_sN_t)$, $(Ti_{0.984}Mo_{0.016})(O_{2-s-t}C_sN_t)$, $(Ti_{0.957}Mo_{0.043})(O_{2-s-t}C_sN_t)$, $(Ti_{0.97}W_{0.03})(O_{2-s-t}C_sN_t)$, $(Ti_{0.95}W_{0.05})(O_{2-s-t}C_sN_t)$, $(Ti_{0.996}V_{0.004})(O_{2-s-t}C_sN_t)$, $(Ti_{0.984}V_{0.016})(O_{2-s-t}C_sN_t)$, or $(Ti_{0.97}V_{0.03})(O_{2-s-t}C_sN_t)$.

Embodiment 26

The heterogeneous material of embodiment 16, wherein the n-type semiconductor comprises $(Ti_{1-r}M_r)(O_{2-s-t}C_sN_t)$, wherein:
  M is Sn;
  r is from 0 to 0.25;
  s is from 0.001 to 0.1; and
  is from 0.001 to 0.1.

Embodiment 27

The heterogeneous material of embodiment 26, wherein r is greater than 0.

Embodiment 28

The heterogeneous material of embodiment 26, wherein r is 0, and the semiconductor comprises a rutile phase and an anatase phase.

Embodiment 29

The heterogeneous material of embodiment 16, wherein the n-type semiconductor is a tin oxide.

Embodiment 30

A method of decomposing a chemical compound, comprising exposing the chemical compound to a photocatalyst comprising the homogeneous material of any of embodiments 1-29 in the presence of light.

Embodiment 31

The method of embodiment 30, wherein the chemical compound is a pollutant.

Embodiment 32

A method of killing a microbe, comprising exposing the microbe to a photocatalyst comprising the homogeneous material of any of embodiments 1-29 in the presence of light.

Embodiment B1

A heterogeneous material comprising:
- a p-type semiconductor comprising a first metal oxide compound and a second metal oxide compound, wherein the first metal oxide compound and the second metal oxide compound have different oxidation states of the same metal, and wherein the p-type semiconductor has a p-type valence band;
- a first n-type semiconductor having an n-type valence band which is deeper than the p-type valence band, wherein the first n-type semiconductor is in ionic charge communication with the p-type semiconductor.

Embodiment B2

The heterogeneous material of embodiment B1, further comprising a second n-type semiconductor.

Embodiment B3

The heterogeneous material of embodiment B1 or B2, wherein the first n-type semiconductor is $TiO_2$.

Embodiment B4

The heterogeneous material of embodiment B1, B2, or B3, wherein the first n-type semiconductor is a combination of anatase $TiO_2$ and rutile $TiO_2$.

Embodiment B5

The heterogeneous material of embodiment B1, B2, B3, or B4, wherein the first n-type semiconductor comprises $WO_3$.

Embodiment B6

The heterogeneous material of embodiment B1, B2, B3, B4, or B5, wherein the molar ratio of the first n-type semiconductor to the second n-type semiconductor is about 0.5 to about 10.

Embodiment B7

The heterogeneous material of embodiment B1, B2, B3, B4, B5, or B6, wherein the second n-type semiconductor is $CeO_2$, $GeO_2$, $SnO_2$, or $ZrO_2$.

Embodiment B8

The heterogeneous material of embodiment B1, B2, B3, B4, B5, B6, or B7, wherein the second n-type semiconductor is $CeO_2$.

Embodiment B9

The heterogeneous material of embodiment B1, B2, B3, B4, B5, B6, B7, or B8, wherein the second n-type semiconductor is $GeO_2$.

Embodiment B10

The heterogeneous material of embodiment B1, B2, B3, B4, B5, B6, B7, B8, or B9, wherein the second n-type semiconductor is $ZrO_2$.

Embodiment B11

The heterogeneous material of embodiment B1, B2, B3, B4, B5, B6, B7, B8, B9, or B10, wherein the p-type semiconductor comprises $Cu_xO$.

Embodiment B12

The heterogeneous material of embodiment B1, B2, B3, B4, B5, B6, B7, B8, B9, B10, or B11 wherein the p-type semiconductor is about 0.001% to about 5% of the heterogeneous material by weight.

Embodiment B13

The heterogeneous material of embodiment B1, B2, B3, B4, B5, B6, B7, B8, B9, B10, B11, or B12, wherein the p-type semiconductor is $Cu_xO$, and is about 0.01% to about 1% of the heterogeneous material by weight.

Embodiment B14

The heterogeneous material of embodiment B1, B2, B3, B4, B5, B6, B7, B8, B9, B10, B11, B12, or B13, wherein at least 50% of the p-type semiconductor is loaded onto the surface of particles of the first n-type semiconductor and particles of the second n-type semiconductor.

Embodiment B15

The heterogeneous material of embodiment B1, B2, B3, B4, B5, B6, B7, B8, B9, B10, B11, B12, B13, or B14, wherein the heterogeneous material is in the form of a powder.

Embodiment B16

A method of preparing a heterogeneous material comprising:

heating a mixture of:
1) a first n-type semiconductor and a second n-type semiconductor; and
2) an aqueous solution comprising a copper ion complex;

wherein the first n-type semiconductor and the second n-type semiconductor are mixed prior to combining the first n-type semiconductor and the second n-type semiconductor with the aqueous solution comprising the copper ion complex.

Embodiment B17

The method of embodiment B16, further comprising filtering the heterogeneous material out of the mixture of the after the mixture has been heated.

Embodiment B18

A method of decomposing a chemical compound, comprising exposing the chemical compound to a photocatalyst comprising the heterogeneous material of embodiment B1, B2, B3, B4, B5, B6, B7, B8, B9, B10, B11, B12, B13, B14, or B15, in the presence of light.

Embodiment B19

The method of embodiment B16, B17, or B18, wherein the chemical compound is a pollutant.

Embodiment B20

A method of killing a microbe, comprising exposing the microbe to a photocatalyst comprising the heterogeneous material of embodiment B1, B2, B3, B4, B5, B6, B7, B8, B9, B10, B11, B12, B13, B14, or B15, in the presence of light.

EXAMPLES

I. Synthesis

Example 1(a). Synthesis of an n-Type Semiconductor (Ex-1)

$Ti(CNO)_2$:Sn (Ex-1): 3.78 g of Tin(II) 2-ethylhexanoate [also known as tin(II) octoate and/or stannous octoate] (Spectrum Chemicals, Gardena, Calif., USA), 30 ml 50 wt % solution of titanium(IV) bis(ammonium lactato)dihydroxide (titanium lactate, [Tyzor LA]) (Sigma Aldrich, St. Louis, Mo., USA) and 15.0 g of ammonium nitrate ($NH_4NO_3$) (Sigma Aldrich, St. Louis, Mo., USA) were dissolved in 25 ml of reverse osmosis (RO) purified water, then heated to 150° C. and stirred for 20 min. The resulting mixture was then heated at 350° C. for 40 min in a preheated muffle furnace under ambient atmosphere (room atmosphere) and pressure conditions. The resulting powder was placed in the preheated muffle furnace and then annealed at 475° C. under ambient conditions for 40 min.

Example 1(b). Loading

Combustion synthesized $Ti(O,C,N)_2$:Sn (6 g) was mixed with 6M HCl (60 mL) at 90° C. for 3 hours in a water bath while stirring. The mixture was then cooled down to room temperature, filtered through 0.2 μm membrane filter paper, washed with 100 to 150 mL of deionized water (DI) water, and finally dried at room temperature overnight for between 10 to 15 h.

The weight fraction of Copper to processed $Ti(O,C,N)_2$:Sn (1 g) was 0.01. 10 mL aqueous solution of $CuCl_2.2H_2O$ (26.8 mg) was stirred with 1 g of processed $Ti(O,C,N)_2$:Sn at 90° C. for 1 hour. Then, 1.5 ml of aqueous solution containing NaOH (50 mg) and glucose (250 mg) was added to the reaction mixture at 90° C. while stirring. After the addition of aqueous solution of glucose and NaOH, the mixture was stirred for another 1 hour, then cooled down to room temperature, followed by filtration through 0.2 μm membrane, washing with 100 to 150 mL DI water and finally dried it at 110° C. in air oven overnight (10 to 15 hour).

The $CuO:Cu_2O$ weight ratio in Ex-1 was determined to be 0.789:0.211. By comparison, a $Cu_xO/TiO_2$ nanocomposite obtained according to the procedure of Qui, et al., ACS Nano, 6, 1609-1618, had a $CuO:Cu_2O$ weight ratio of 0.169:0.831.

Example 1(b)'. Comparative Example 0 (CE-0)

Total weight percent of Cu as 0.25 wt % CuO+0.125 wt % $Cu_2O$ was physically mixed with Sn—$Ti(OCN)_2$ photocatalyst by hand using mortar and pestle in 5-10 mL of methanol. The mixing was continued until all the methanol had evaporated.

Example 1(c). Comparative Example 1 (CE-1)

CE-1 ($Ti(CNO)_2$:Sn) was prepared in a manner similar to that of Example 1(a), except that no loading of $Cu_xO$ (step A only) was performed resulting in unloaded $Ti(CNO)_2$:Sn (no $Cu_xO$).

Example 1(d). Comparative Example 2 (Ex-1A)

Ex-1A was prepared in a manner similar to that of Example 1(b) above, except that 25 mg instead of 50 mg of NaOH and 125 mg instead of 250 mg of glucose were used.

Example 1(d)'. Comparative Example 2' (Ex-1B)

Ex-1B was prepared in a manner similar to that of Example 1(b) above, except that the weight fraction of Copper to processed $Ti(O,C,N)_2$:Sn (1 g) was 0.005.
Example 1(e). Comparative Example 3 (Ex-2 and Ex-3)

Ex-2 (Plasma $WO_3$) and Ex-3 (commercial GTP $WO_3$) were prepared in a manner similar to that of Ex-1 above, except that the same molar amounts of Plasma $WO_3$ or commercial GTP-$WO_3$ were used instead of $Ti(O,C,N)_2$:Sn photocatalyst; NaOH was not added to the reaction mixture and the glucose amount was 125 mg instead of 250 mg. Plasma $WO_3$ was made in a similar manner to that described in U.S. patent application Ser. No. 13/738,243, filed Jan. 10, 2013 which is incorporated by reference herein for its teachings regarding the same. GTP $WO_3$ was purchased from Global Tungsten & Powder (Towanda, Pa., USA) and used without additional purification or annealing.

0.159 mL of 1M Bis(Ethylenediamine) copper(II) hydroxide was mixed with 10 mL of RO water and it was stirred with 1 g of $WO_3$ at 90° C. for 1 h. Then, glucose (125 mg) was added to the reaction mixture at 90° C. while stirring. After the addition of the aqueous solution of glucose the mixture was stirred for another 1 hour, then cooled down to room temperature, followed by filtration through 0.2 μm membrane, washing with 100 to 150 mL DI water and finally dried it at 110° C. in air oven overnight (10 to 15 h).

Example 1(f). Comparative Example 4 (Ex-4, Ex-5, Ex-6, CE-2)

Ex-4, Ex-5, Ex-6 and CE-2 were prepared in a manner similar to that of Ex-1, except that the same molar amounts of $CeO_2$ were used instead of $Ti(O,C,N)_2$:Sn. In addition, the loading conditions were modified as follows: Ex-4: aqueous solution of NaOH (25 mg) and glucose (125 mg); Ex-5: without glucose; Ex-6: the concentration of glucose (62.5 mg) and NaOH (25 mg).

CE-2 is analogous to CE-1, except that CE-2 is an equivalent unloaded molar amount (to $Ti(O,C,N)_2$:Sn) of $CeO_2$ (Sigma Aldrich, St. Louis, Mo., USA). $CeO_2$ was used as received from the vendor without additional purification or annealing.

Example 1(g). Comparative Example 5 (Ex-7, CE-3)

Ex-7 was prepared in a manner similar to that of Ex-1 above, except that the same molar amount of insulator, $Al_2O_3$ was used instead of $Ti(O,C,N)_2$:Sn, 25 mg of NaOH was used, and 125 mg of glucose was used. The $Cu_xO$ loading was 1 wt % Cu with respect to $Al_2O_3$. CE-3 is analogous to CE-1, except that CE-3 is an equivalent unloaded molar amount (to $Ti(O,C,N)_2$:Sn) of $Al_2O_3$. $Al_2O_3$ was used as received from the vendor without additional purification or annealing.

Example 1(h). Comparative Example 6 (Ex-8, CE-4)

Ex-8 was prepared in a manner similar to that of Ex-1 above, except that the same molar amount of n-type UV active photocatalyst, $Ta_2O_5$ was used instead of $Ti(O,C,N)_2$:Sn, 25 mg of NaOH and 125 mg of glucose were used. The $Cu_xO$ loading was 1 wt % Cu with respect to $Ta_2O_5$. CE-4 is analogous to CE-1, except that CE-4 is an equivalent unloaded molar amount (to $Ti(O,C,N)_2$:Sn) of $Ta_2O_5$ (Sigma Aldrich, St. Louis, Mo., USA). $Ta_2O_5$ was used as received from the vendor without additional purification or annealing.

Example 1(i). Comparative Example 7 (Ex-9, Ex-10, Ex-11, Ex-19, Ex-20, CE-4A)

Ex-9 was prepared in a manner similar to that of Ex-1 above, except that the same amount of n-type UV active photocatalyst, $SnO_2$ was used instead of $Ti(O,C,N)_2$:Sn. The $Cu_xO$ loading was 1 wt % Cu with respect to $SnO_2$. The nanosize $SnO_2$ (US Research Nanomaterial, Houston, Tex., USA) had been annealed at 900° C. in a box furnace in air for 1 h. It was then soaked in 6M HCl aqueous solution as in Ex-1. In Ex-10, the amount of NaOH was 25 mg and the amount of glucose used was 125 mg. In Ex-11, the amount of NaOH was 75 mg and the amount of glucose was 375 mg. In Ex-19 and Ex-20 the annealed $SnO_2$ was not soaked in 6M HCl aqueous solution as in Ex-1, Ex-10, Ex-11. In Ex-19, the amount of NaOH was 25 mg and the amount of glucose used was 3 mg. In Ex-20, the amount of NaOH was 25 mg and the amount of glucose was 10 mg. CE-4A is analogous to CE-1, except that CE-4A is an equivalent unloaded molar amount (to $Ti(O,C,N)_2$:Sn) of $SnO2$. With varying amounts of NaOH and glucose while loading fixed amount of 1 wt % Cu with respect of $SnO_2$, different appearances of body color resulted.

Example 1(j). Comparative Example 8 (Ex-12, CE-5, Ex-13)

Ex-12 was prepared in a manner similar to that of Ex-1B above. Loading of $Cu_xO$ was performed on rutile $TiO_2$ (Tayca, Inc. Osaka, JP) except that 25 mg instead of 50 mg of NaOH and 125 mg instead of 250 mg of glucose were used.

CE-5 is analogous to CE-1, except that CE-5 is an equivalent unloaded molar amount (to $Ti(O,C,N)_2$:Sn) of Rutile TiO2 (Tayca, Inc. Osaka, JP). Rutile TiO2 was used as received from the vendor without additional purification or annealing.

For Ex-13, 10 g commercial $WO_3$ (Global Tungsten Powder, Sylvania, Pa., USA) was annealed at 400° C. for 1 h. $[Pt(NH_3)_4]Cl_2$ (0.181 mg Alfa Aesar, Ward Hill, Mass., USA)] was dissolved in 15.0 mL RO water and stirred with 2.0 g of the annealed $WO_3$ at room temperature (RT) for 2 h. Then, it was filtered through membrane filter paper of pore size 0.2 μm and washed with RO water and dried at 120° C. overnight. The resulting material was annealed at 400° C. for another 1 h in air.

Example 1(k). Comparative Example 9 (Ex-13-17, CE-6)

Ex-14 to Ex-17 were prepared in a manner similar those described above except that different amounts of $[Pt(NH_3)_4]Cl_2$ and/or $IrCl_3/IrO_2$ were dissolved in the 15 mL of RO water. See Table 1 as follows:

TABLE 1

| Example | Amount $[Pt(NH_3)_4]Cl_2$ | Wt % $[Pt(NH_3)_4]Cl_2$ | Amount $IrCl_3$ | Wt % $IrCl_3$ | Amount $WO_3$ |
|---|---|---|---|---|---|
| Ex-13 | 1.44 mg | 0.05 wt % | 0 mg | 0.00 wt % | 2 g |
| Ex-14 | 2.88 mg | 0.1 wt % | 0 mg | 0.00 wt % | 2 g |
| Ex-15 | 5.76 mg | 0.2 wt % | 0 mg | 0.00 wt % | 2 g |
| Ex-16 | 0 mg | 0.00 wt % | 3.046 mg | 0.1 wt. % $IrO_2$ | 2 g |
| Ex-17 | 0.144 mg | 0.05 wt % | 3.046 mg | 0.1 wt. % $IrO_2$ | 2 g |
| CE-6 | 0.00 mg | 0.00 wt % | 0.00 mg | 0.00 wt % | 2 g |

CE-6 is analogous to CE-1, except that CE-5 is an equivalent unloaded molar amount (to $Ti(O,C,N)_2$:Sn) of $WO_3$ (Global Tungsten Powder, PA, USA). $WO_3$ was used as received from the vendor without additional purification or annealing.

Example 1(l). Synthesis of an N-Type Semiconductor (Ex-18)

MgTi2O5 synthesis: 2.663 g $Mg(NO_3)_2.6H_2O$ (Sigma Aldrich, St. Louis, Mo., USA), 5 g ammonium nitrate (Sigma Aldrich, St. Louis, Mo., USA), 1.5 g urea (Sigma Aldrich, St. Louis, Mo., USA) and 10 mL of titanium(IV) bis(ammonium lactate)hydroxide (titanium lactate, [Tyzor LA]) (Sigma Aldrich, St. Louis, Mo., USA) were dissolved in about 10 mL of DI water in 250 mL of low-form Pyrex® beaker. The resulting mixture was then heated at 350° C. for 20 min in a preheated muffle furnace under ambient atmosphere (room atmosphere) and pressure conditions. The resulting powder was placed in the preheated muffle furnace and then annealed at 600° C. under ambient conditions for about 30 min.

$Cu_xO$ Loaded $MgTi_2O_5$: $Cu_xO$ was loaded onto the $MgTi_2O_5$ in a manner similar to that described in Example 1(b), except that in this preparation, no HCl preparation step was used. The NaOH preparation step used was similar to that described in Example 1(b). The weight fraction of copper to $MgTi_2O_5$ was 0.01. 10 mL aqueous solution of $CuCl_2.2H_2O$ (26.8 mg) was stirred with 1 g of $MgTi_2O_5$ at about 90° C. for about 1 h. Then, 1.5 mL of aqueous solution containing NaOH(25 mg) and glucose (125 mg) was added to the reaction mixture at about 90° C. while stirring. After the addition of aqueous solution of glucose and NaOH, the mixture was stirred for about another 1 h, then cooled down to room temperature, followed by filtration through 0.05 μm membrane, washing with 100 to 150 mL DI water and finally dried it at 110° C. in air oven for about 2 h.

Example 1(m). (Ex-20 ($Cu_xO$ Loaded Plural Phase $TiO_2$))

The plural phasic n-type semiconductor was loaded onto CuxO in a manner similar to that in Example 1(b). The weight fraction of copper to plural phasic n-type semiconductor (87% anatase phase TiO2/13% rutile phase $TiO_2$ sold under the brand name P25™ [Evonik Degussa, NJ, USA]) was 0.01. 15 mL aqueous solution of $CuCl_2.2H_2O$ (26.8 mg) was stirred with 1 g of P25™ at about 90° C. for 1 h. Then, 1.5 mL of aqueous solution containing NaOH (25 mg) and glucose (125 mg) was added to the reaction mixture at about 90° C. while stirring. After the addition of aqueous solution of glucose and NaOH, the mixture was stirred for about another 1 h, then cooled down to room temperature, followed by filtration through 0.05 μm membrane, washing with 100 to 150 mL DI water and finally dried it at 110° C. in air oven for about 2 h.

Example 1(n). (CE-7)

Comparative Example CE-7 was prepared in a manner similar to Example 1(m) except that 0.25 wt. % CuO+0.125 wt. % $Cu_2O$ was physically mixed with 0.625 wt % P25™ in methanol (5-10 mL) by hand until the methanol was substantially all evaporated.

Example 1(o). (Ex-19 ($AgVWO_6$))

4.12 g of vanadyl oxalate (Stratcor, Inc, Arkansas, USA), 0.3 g glycine (Sigma Aldrich, St. Louis, Mo., USA), 0.62 g ammonium nitrate (Sigma Aldrich, St. Louis, Mo., USA) and 1.484 g ammonium metatungstate (Global Tungsten & Powder, PA, USA) were dissolved in about 5 mL of reverse osmosis (RO) purified water. To this solution 1 g silver nitrate (Alfa Aesar, Ward Hill, Mass., USA) was added to get brownish slurry in 250 mL low form beaker, then, the resulting mixture was then heated at about 350° C. for about 20 min in a preheated muffle furnace under ambient atmosphere (room atmosphere) and pressure conditions. The resulting powder was placed in the preheated muffle furnace and then, annealed at about 500° C. under ambient conditions for about 60 minutes, which has resulted in yellow powder (Ex-19).

Example 1(p). (Ex-20 ($AgCa_2Zn_2V_3O_{12}$))

6.19 g of vanadyl oxalate (Stratcor, Inc, Hot Springs, Ark., USA), 1.11 g glycine (Sigma Aldrich, St. Louis, Mo., USA), 1.75 g zinc nitrate hexahydrate (Sigma Aldrich, St. Louis, Mo., USA), 1.39 g calcium nitrate tetrahydrate (Sigma Aldrich, St. Louis, Mo., USA), 2.49 g ammonium nitrate (Sigma Aldrich, St. Louis, Mo., USA) were dissolved in about 10 mL of reverse osmosis (RO) purified water. To this solution 0.5105 g silver nitrate (Alfa Aesar, Ward Hill, Mass., USA) was added to get brownish slurry in 250 mL low form glass beaker, then, the resulting mixture was then heated at about 350° C. for about 20 min in a preheated muffle furnace under ambient atmosphere (room atmosphere) and pressure conditions. The resulting powder was placed in the preheated muffle furnace and then, annealed at about 600° C. under ambient conditions for about 60 minutes, which resulted in yellow powder (Ex-20).

Example 1(q). (Ex-21 ($Ag_3PO_4$))

5 g of silver nitrate (Alfa Aesar, Ward Hill, Mass., USA) was dissolved in 10 mL of reverse osmosis (RO) purified water in 50 mL glass beaker. In a separate 50 mL glass beaker, 1.128 g of ammonium dihydrogen phosphate (Sigma Aldrich, St. Louis, Mo., USA) was dissolved in 10 mL of reverse osmosis (RO) purified water. To the aqueous solution of ammonium dihydrogen phosphate aqueous solution of silver nitrate was added drop by drop while stirring the ammonium dihydrogen phosphate solution. The yellow precipitate formed during this addition at room temperature was finally filtered and dried at 110° C. for 2 h in an air oven.

Example 2. Characterization of Supported P-Cats

Example 2(a). Powder XRD Characterization (Ex-1A, CE-1, Ex-4, CE-2, Ex-7 and CE-3)

Figure 3:
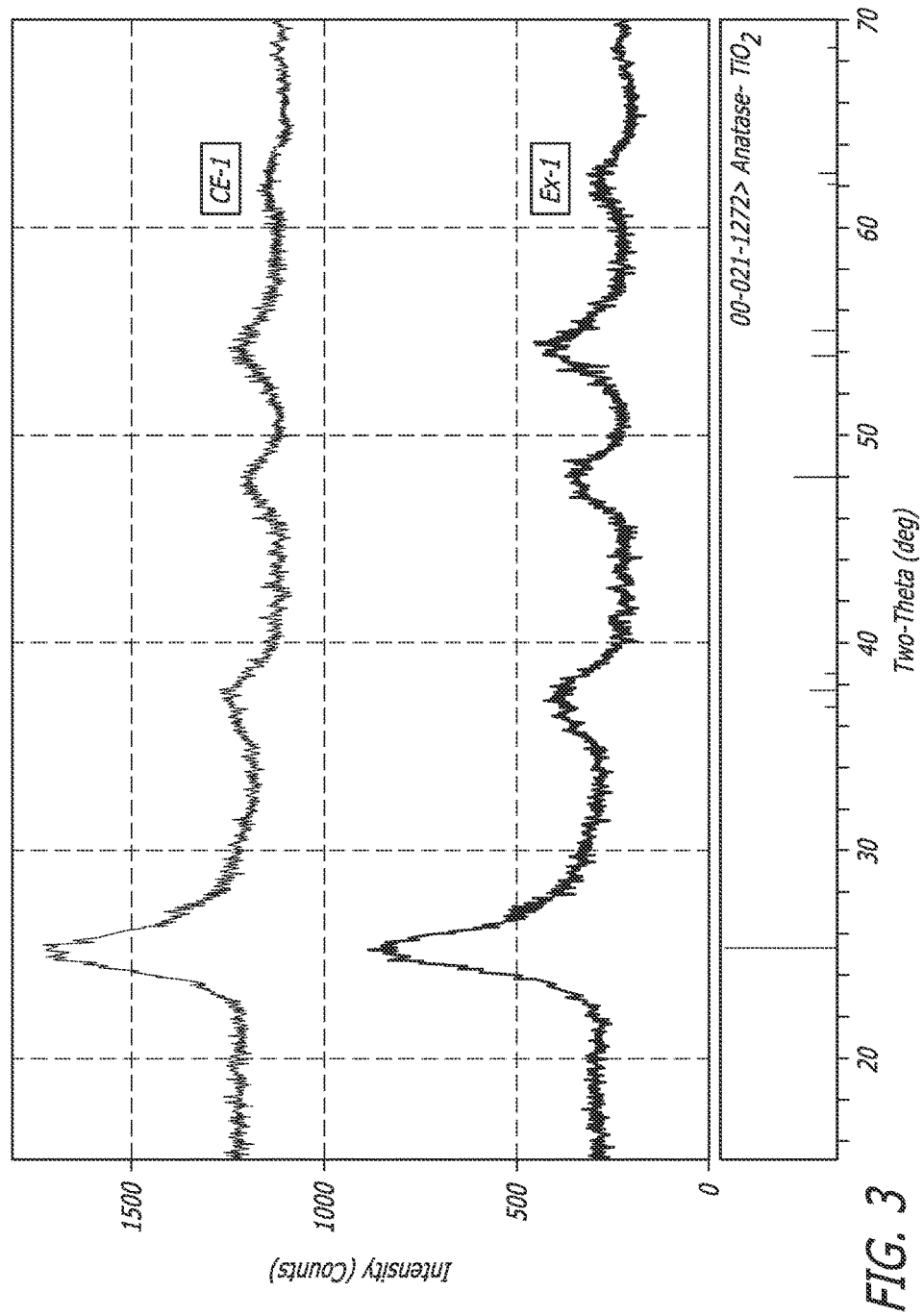
FIG. 3 shows the x-ray diffraction patterns of an embodiment of a p-type and n-type composite material described herein with that of the n-type material alone.

Powder samples of Ex-1A, CE-1, Ex-4, CE-2, Ex-7 and CE-3 were analyzed using powder x-ray diffraction using Cu K-alpha radiation (Rigaku Miniflex II™ [Rigaku Americas, Woodland, Tex., USA]) with Vimin. The result of the x-ray diffraction analysis of Ex-1 and CE-1 is shown in FIG. 3 and confirms the presence of anatase $TiO_2$. It was confirmed from XRD patterns (FIG. 3) that the anatase phase of Ti(O,C,N)2:Sn is retained even after $Cu_xO$ loading because comparison of the resulting XRD spectrogram with joint committed powder diffraction standards, card no. 00-021-1272 [anatase-TiO2] (JCPDS) by International Centre for Diffraction Data (Newton Square, Pa., USA) exhibits substantially the same peaks as the anatase phase spectrogram (the phase of the material generally visible light photocatalytically active).

Figure 4:
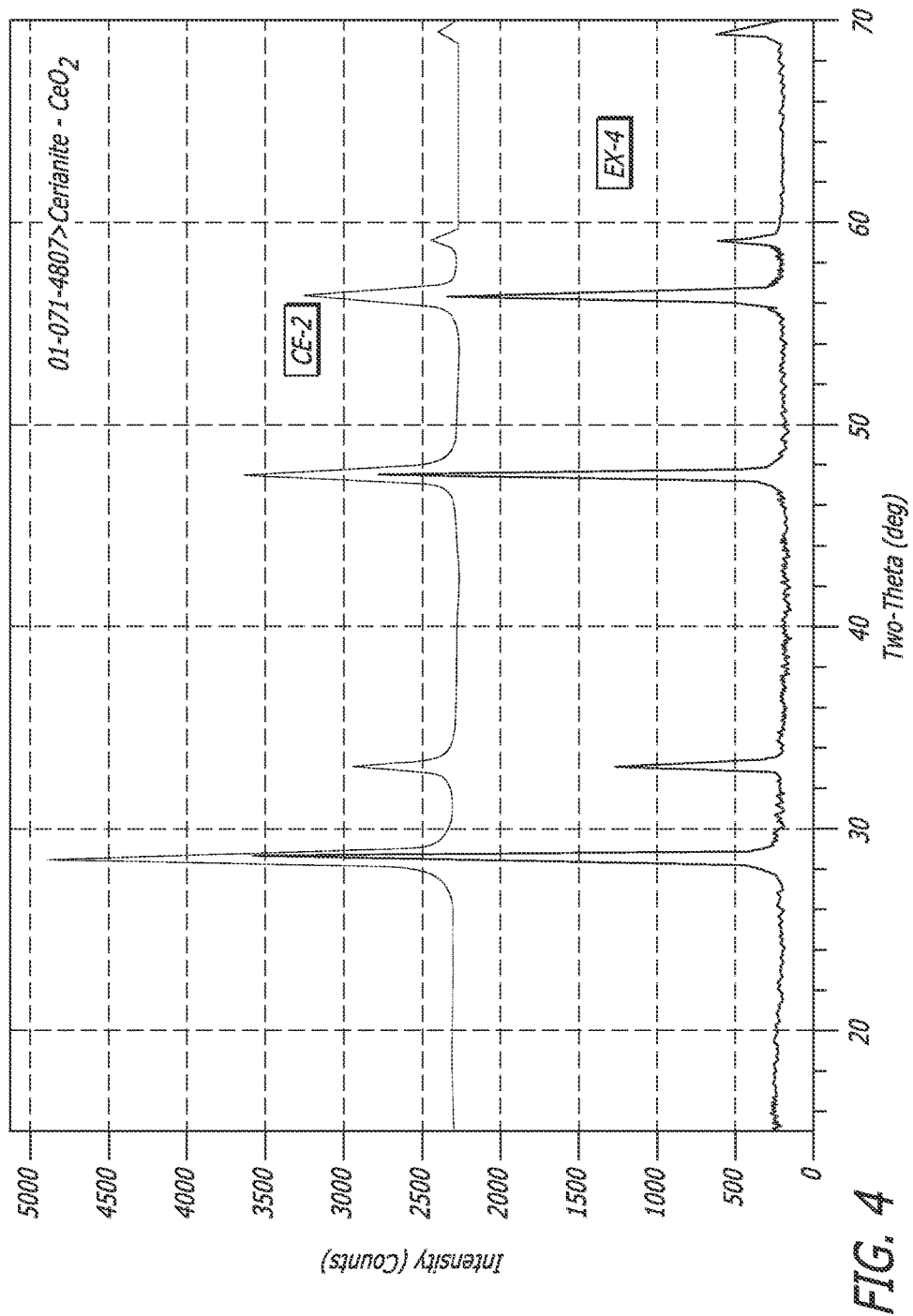
FIG. 4 shows the x-ray diffraction patterns of another embodiment of a p-type and n-type composite material described herein with that of the n-type material alone.
Figure 5:
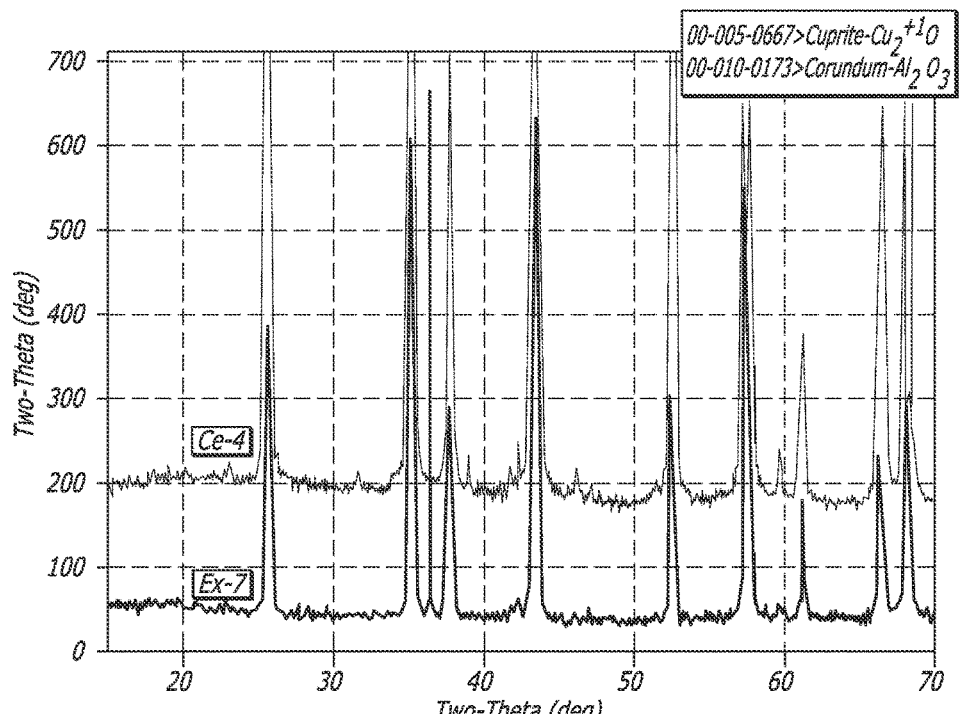
FIG. 5 shows the x-ray diffraction patterns of another embodiment of a p-type and n-type composite material described herein with that of the n-type material alone.
Figure 6:
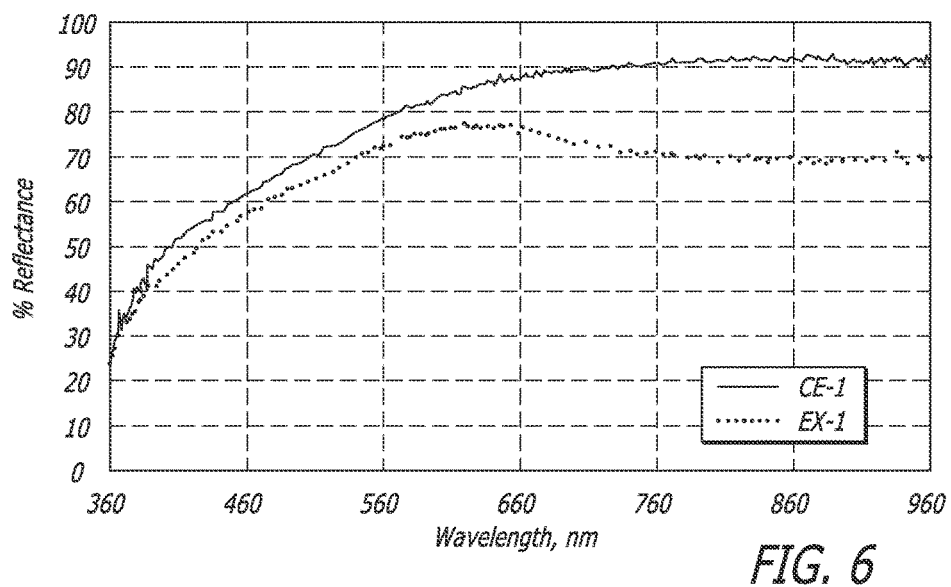
FIG. 6 shows the diffuse reflectance spectra comparing embodiments of a p-type and n-type composite material described herein and that of the n-type material alone ($Ti(OCN)_2$:Sn).
Figure 7:
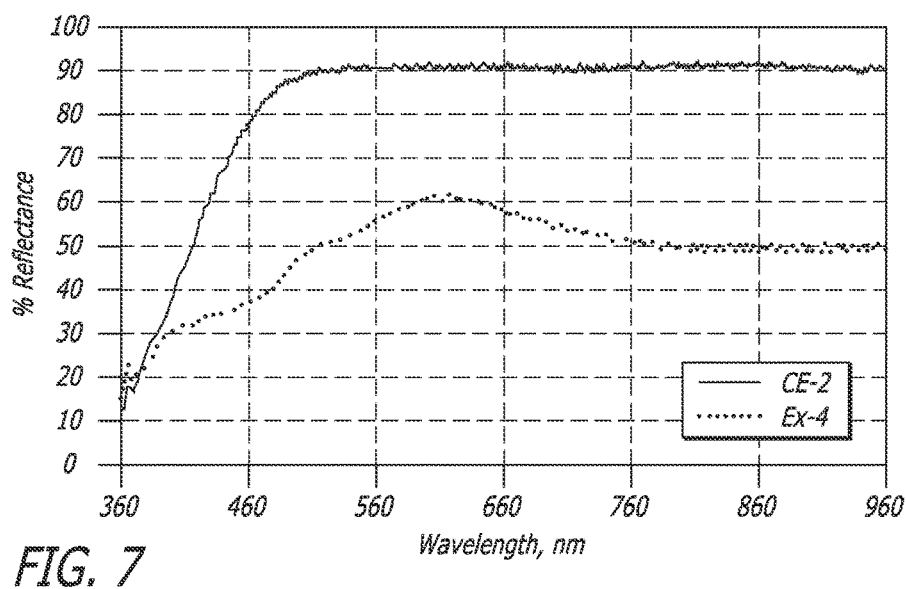
FIG. 7 shows the diffuse reflectance spectra comparing another embodiment of a p-type and n-type composite material described herein that of the n-type material alone ($CeO_2$).
Figure 8:
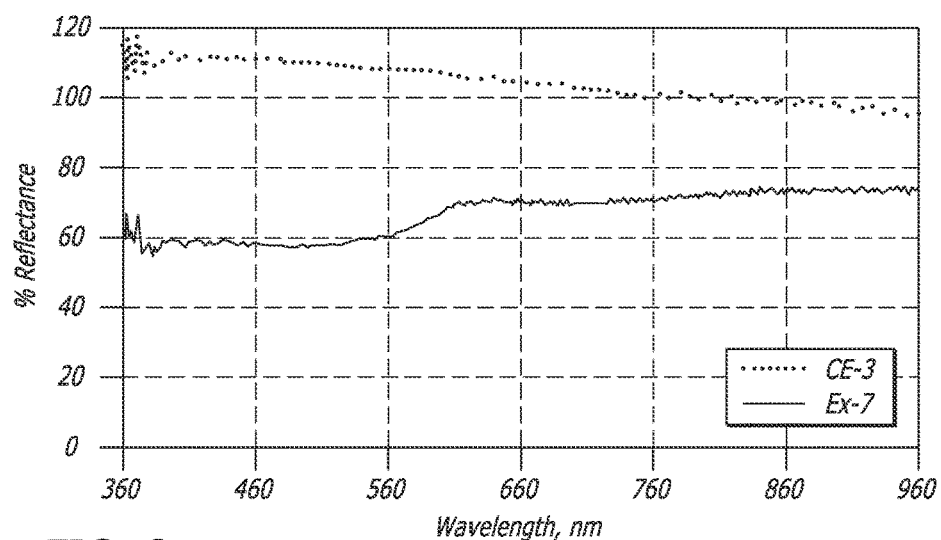
FIG. 8 shows the diffuse reflectance spectra comparing another embodiment of a p-type and n-type composite material described herein that of the n-type material alone.

In addition, powder samples of Ex-4 and Ex-7 were analyzed in a manner similar to that of Ex-1A above, except that equal molar amounts of Ex-4 and Ex7 were used instead of Ex-1A. The results are shown in FIGS. 4 and 5, respectively-using powder x-ray diffraction using Cu K-alpha radiation (Rigaku Miniflex II™ [Rigaku Americas, Woodland, Tex., USA) with 1°/min. The result of the X-ray diffraction shown in FIGS. 4 and 5 confirms the $Cu_xO$ loading did not substantially affect the bulk semiconducting phase of the respective n-type material Example 2(b). DRS Characterization Powder samples of Ex-1A, CE-1 (FIG. 6); Ex-4 and CE-2 (FIG. 7), Ex-7 and CE-3 (FIG. 8) were analyzed using diffuse reflectance spectroscopy (DRS). The results are shown in FIGS. 6, 7 and 8, and indicate that at least tin doping (Ex-1A), $CeO_2$ (Ex-4) and $Al_2O_3$(Ex-7) appeared to improve absorption in the visible spectrum (400 nm to 800 nm), whereas CE-1, CE-2 and CE-3 did not. Therefore, the anatase $TiO_2$ observed in the XRD pattern and visible absorption due to the anatase phase confirmed the loading of $Ti(O,C,N)_2$:Sn, $CeO_2$, and $Al_2O_3$ on the substrate. The loaded $Cu_xO$ had absorption in the longer wavelength side of absorption edge of semiconductors and if the loaded $Cu_xO$ had a mixture of CuO and $Cu_2O$, then their characteristics absorptions between 600 and 800 nm and 500 and 600 nm respectively would have been observed, in addition to absorption of loaded $Cu_xO$.

Example 3. Experimental Set-Up for Photocatalysis (Ex-1A and CE-1)

Ex-1A (130 mg), as prepared according to the methods described earlier in this disclosure, was added to 1.04 mL DI water in order to make a coating solution which was 10 wt % solid materials in water. The resulting dispersion was homogenized using an ultrasonic homogenizer. A glass substrate (50 mm×75 mm) was coated with the prepared resultant by using a spin coater (1200 rpm/40 sec). The coated substrate was heated for 2 min at 120° C. Another slide was prepared in the same manner except that CE-1 (130 mg) was used instead of Ex-1A.

Figure 9:
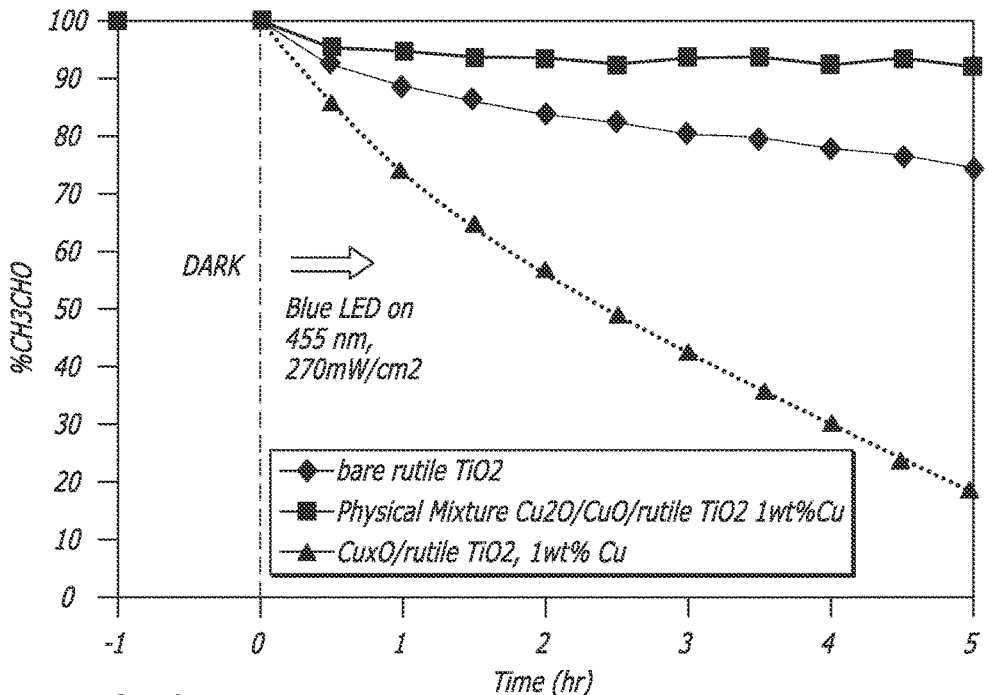
FIG. 9 is a graph showing the decomposition of acetylaldehyde by various photocatalytic composites, Ex-1A and CE-1 described herein.

The spin coated glass slides were heated at 120° C. on a hot plate under full spectrum irradiation by a Xe (xenon) lamp (lamp power output 300 W) for 1 h. Each slide was then sealed in a separate 5 L Tedlar® bag under vacuum, followed by injecting 3 L of ambient air and 80 mL of 3500 ppm acetaldehyde. Each bag was lightly massaged for 2 min by hand then placed in the dark for 15 min. The acetaldehyde concentration was estimated by Gas Chromatography-Flame Ionization Detector (GC-FID) to be at 80±2 ppm. Each Tedlar® bag containing a sample was placed back in the dark for 1 h. The slide/Tedlar® bag was exposed to array blue LED of 455 nm with light intensity of 270 mW/cm². A sample was collected every 30 min by an automated injection port of GC-FID and the amount of remaining acetaldehyde was estimated at subsequent 30 min intervals. FIG. 9 is a graph illustrating Ex-1A VOC performance data. The graph shows that generally when $Ti(CNO)_2$:Sn is combined with CuO (Ex-1A), performance is improved when compared to bare $Ti(CNO)_2$:Sn (CE-1).

Example 4. Antibacterial Experiments

Example 4(a)

Substrate (1"×2" glass slide) was prepared by sequential application of 70% IPA (Isopropyl Alcohol) and 100% ethanol (EtOH) and then dried in air. Ex-1B was dispersed in 100% EtOH at 2 mg/mL concentration and then 100 μL of the suspension was applied to the substrate, and then dried. The application process was repeated 5 times to attain 1 mg of Ex-1B on the substrate. The substrate was then dried at room temperature. The coated substrates were placed in a glass dish with a water soaked filter paper for maintaining moisture, and glass spacers were inserted between the substrate and the filter paper to separate them.

E. coli (ATCC 8739) was streaked onto a 10 cm diameter petri dish containing 20 mL of LB (lysogeny broth/luria broth) agar, and incubated at 37° C. overnight. For each experiment, a single colony was picked to inoculate 3 mL nutrient broth, and the inoculated culture was incubated at 37° C. for 16 h to create an overnight culture (~109 cells/mL). A fresh log-phase culture of the overnight culture was obtained by diluting the overnight culture 100×, inoculating another 5 cm petri dish with LB agar and incubating at 37° C. for 2.5 hr. The fresh culture was diluted 50× with 0.85% saline, which gave a cell suspension of $2\times10^6$ cells/mL. 50 μL of the cell suspension was pipetted onto each deposited glass substrate. A sterilized (in 70% and then 100% EtOH) plastic film (20 mm×40 mm) was placed over the suspension to spread evenly under the film. The specimen was kept in the dark ($Cu_xO_2$-Dark) and then irradiated under blue LED light (455 nm, 10 mW/cm2) ($CuO_2$-light). At chosen time points, e.g., 30 min/60 min increments, the specimen was placed in 10 mL of 0.85% saline and vortexed to wash off the bacteria. The wash off suspension was retained, then serially diluted using 0.85% saline, and then plated on LB agar and incubated at 37° C. overnight to determine the number of viable cells in terms of CFU/Specimen.

Figure 10:
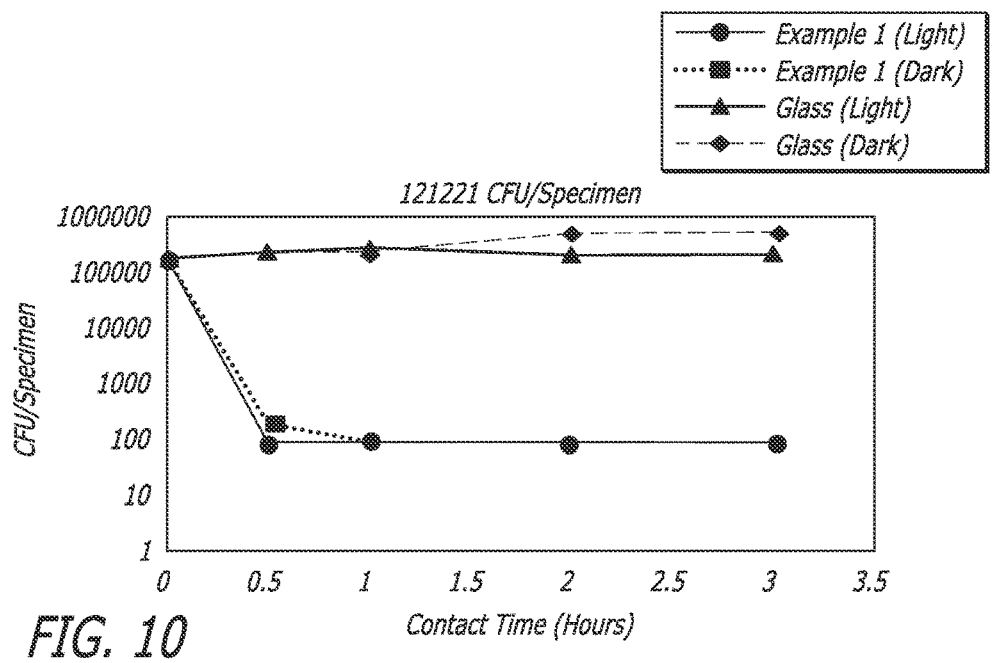
FIG. 10 is a graph showing the antibacterial activity (CFU/Specimen) on $E.\ coli$ by various photocatystic composites, Ex-1A and CE-1 described herein after exposure to visible light of 800 lux from a fluorescent lamp.
Figure 11:
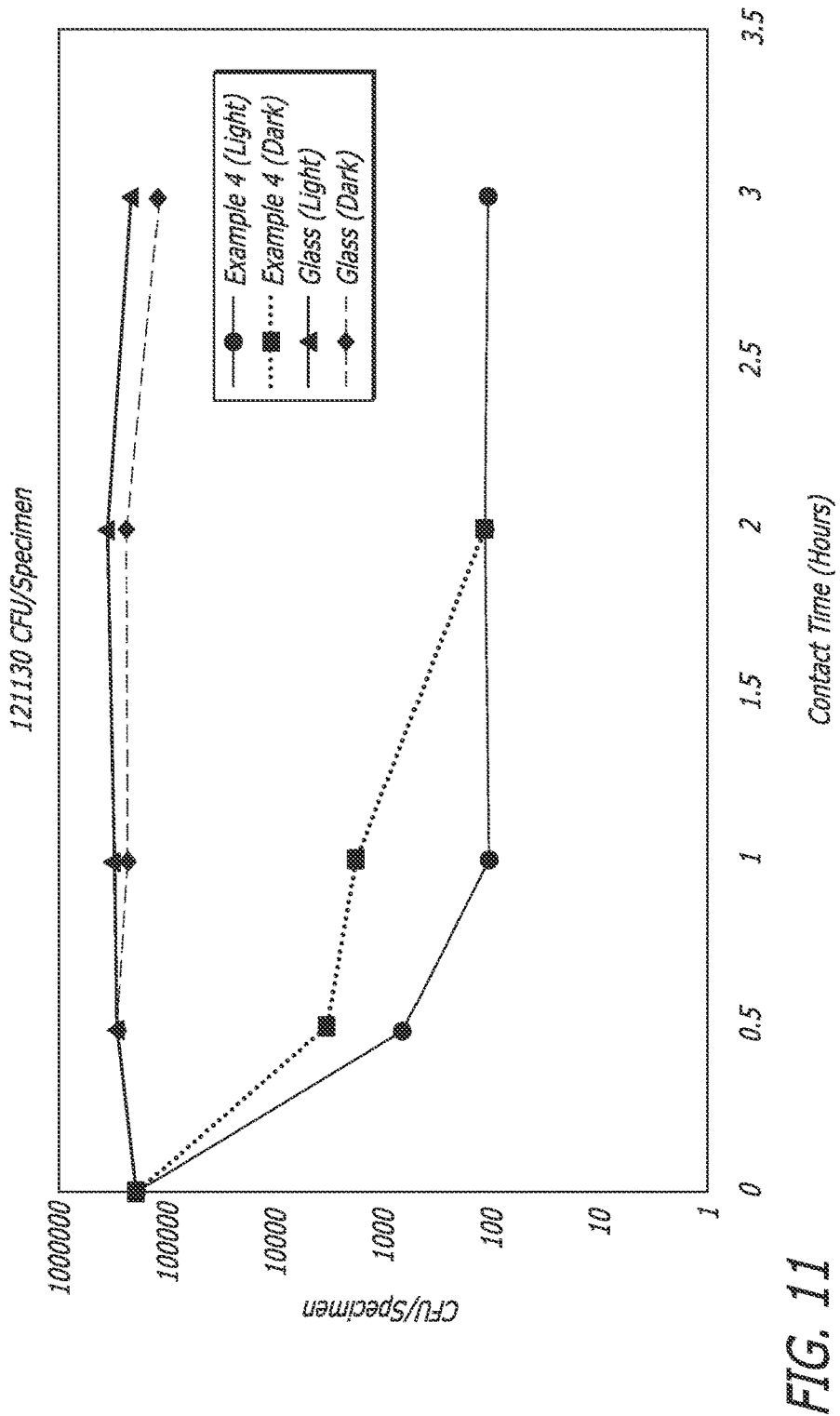
FIG. 11 is a graph showing the antibacterial activity (CFU/Specimen) on $E.\ coli$ by various photocatalytic composites, Ex-4 and CE-2 described herein after exposure to visible light of 800 lux from a fluorescent lamp.

The results are shown in FIGS. 10 and 11. The antibacterial property appears to be due to the presence of flexible copper ion and was observed even in the dark within 30 min of the start of the experiment (See FIGS. 10 and 11).

FIG. 10 also shows the antibacterial property of $Cu^{1+}$ after being loaded on $CeO_2$. The reduction of viable E. coli is observed after 1 h for dark as well as under 10 mW/cm² blue LED of 455 nm light. Therefore, $Cu_xO$ loaded $CeO_2$ is a functional antibacterial material.

Example 4(b)

Figure 12A:
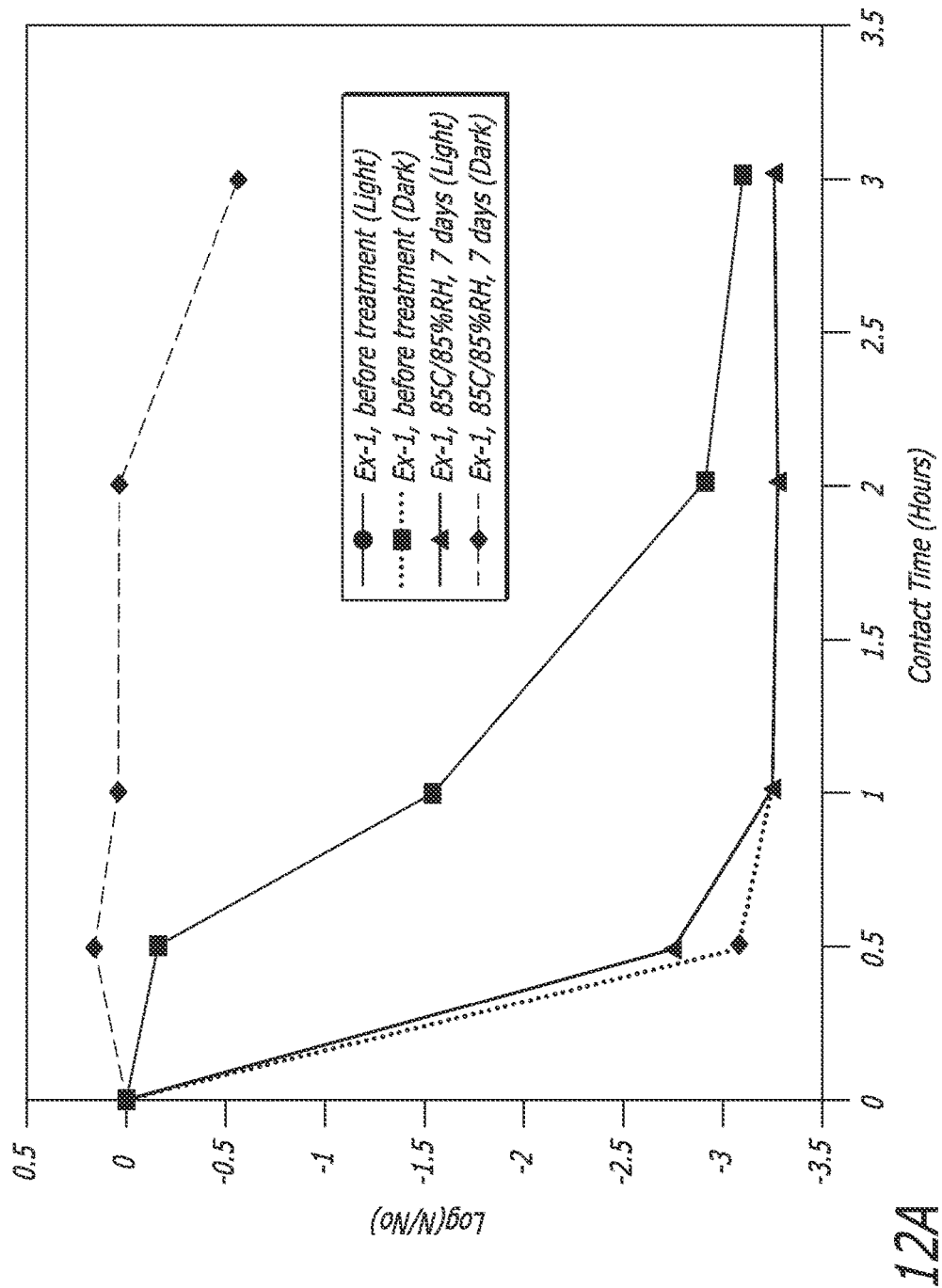
FIG. 12A is a graph showing the enhanced durability antibacterial activity on $E.\ coli$ by photocatalytic composites, Ex-1, before and after being treated at 85° C. and 85% relative humidity (RH) for 7 days.

Ex-1 powder was prepared as described in Example 1. The powder was then kept in the dark at 85% relative humidity and 85° C. for a period of 7 d. The slide[s] were then prepared and tested for antibacterial activity in the same manner as described in Example 4A. The results are shown in FIG. 12A. The results show that even after exposure to 85% relative humidity and 85° C. for a period of 7 d, Ex-1 demonstrated retained photocatalytic activity.

Example 4(c)

Figure 12B:
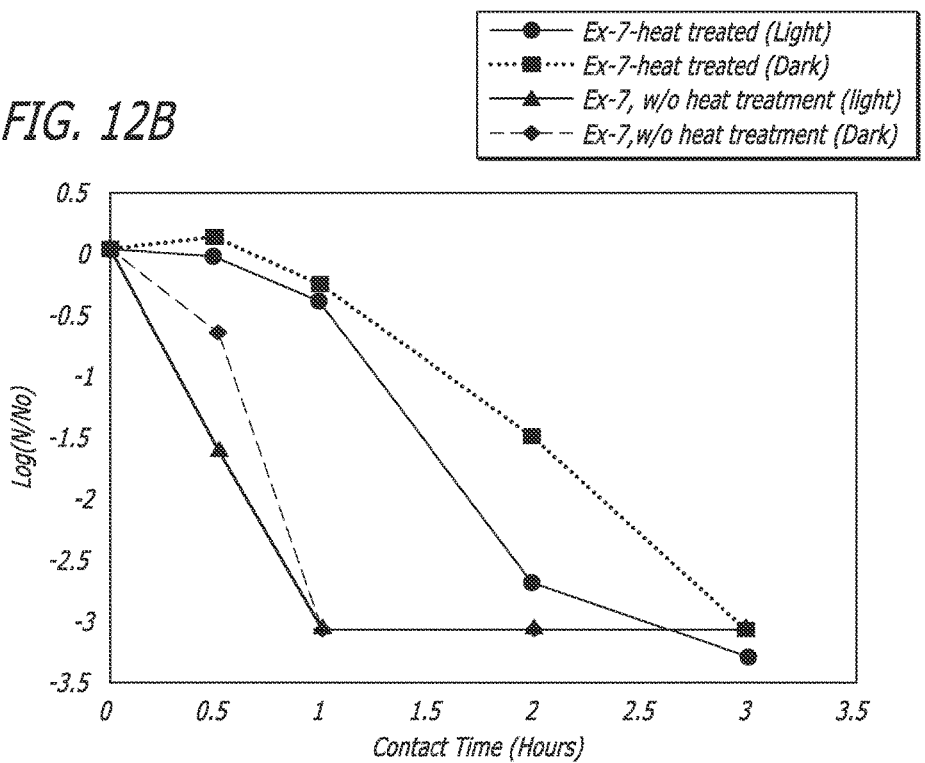
FIG. 12B is a graph showing the enhanced durability antibacterial activity on $E.\ coli$ by photocatalytic composites, Ex-7, before and after treated at 300° C. for 20 min.

Ex-7 powder was prepared as described above. The powder was then kept in the dark at 300° C. for 20 min. The slide[s] were then prepared and tested for antibacterial activity in the same manner as described in Example 4A. The results are shown in FIG. 12B. The results show that even after exposure to 300° C. for 20 min, Ex-7 retained photocatalytic activity.

Example 5. Photocatalysis Experiments for Dye Discoloration Studies

Example 5(a)

Figure 13:
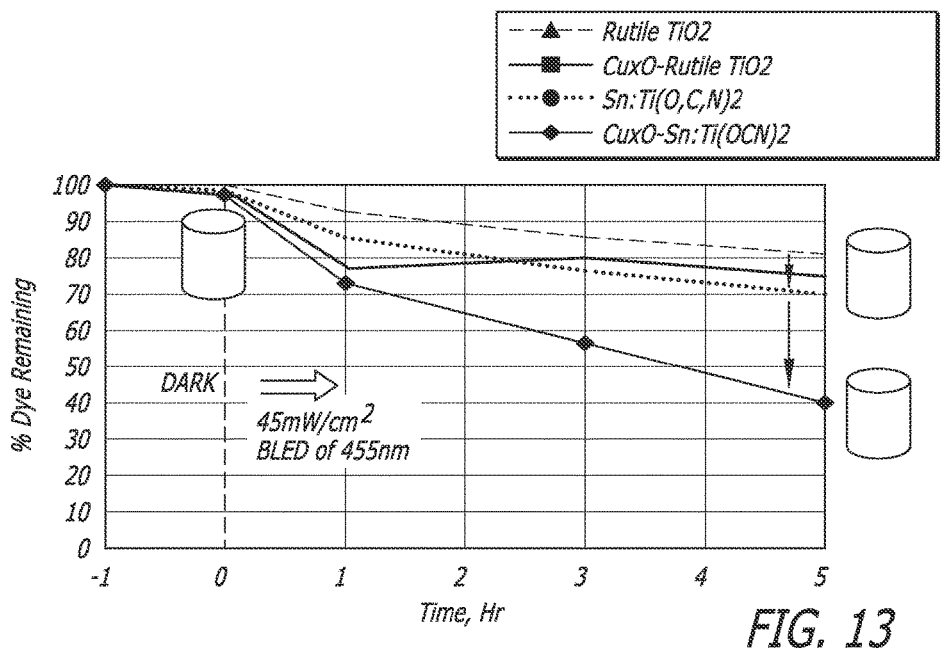
FIG. 13 is a graph showing the dye discoloration of natural blue color by various photocatalytic composites, Example 1 and CE-1 described herein along with rutile $TiO_2$ with and without $Cu_xO$ loading.

The photocatalytic properties for Ex-1, CE-1 and rutile $TiO_2$ loaded with and without $Cu_xO$ were compared by measuring the degradation of food additive dye (natural blue colored powder, Color Maker, Anaheim, Calif., USA) as natural blue color powder 2.85 g of the natural blue color powder was dissolved in 100 mL of RO water creating a blue powder stock solution. 150 mg of each sample was placed in RO water (27 mL) with natural blue color 3 mL of blue powder stack solution for 1 h without any light and then exposed to a blue light emitting diode (455 nm, 45 mW/cm²) for 5 h. The degradation of the resulting blue colored solution was measured at 1 h, 3 h and 5 h by monitoring its concentration using UV-Vis absorption spectroscopy (Cary® 50, Spectrophotometer Agilent Technologies, Santa Clara, Calif., USA). The concentration was calculated as intensity of the peak at 600 nm. The results are shown in FIG. 13. Table 2 below compares the final degradation results of the four photocatalytic materials.

TABLE 2

Comparison of final dye discoloration results by four different photocatalysts.

| Pcat | % dye lost after 5 h under 455 nm blue LED w/ 45 mw/cm$^2$ |
|---|---|
| CE-5 | 19% |
| EX-12 | 25% |
| CE-1 | 31% |
| Ex-1b | 60% |

Example 5(b)

Figure 17:
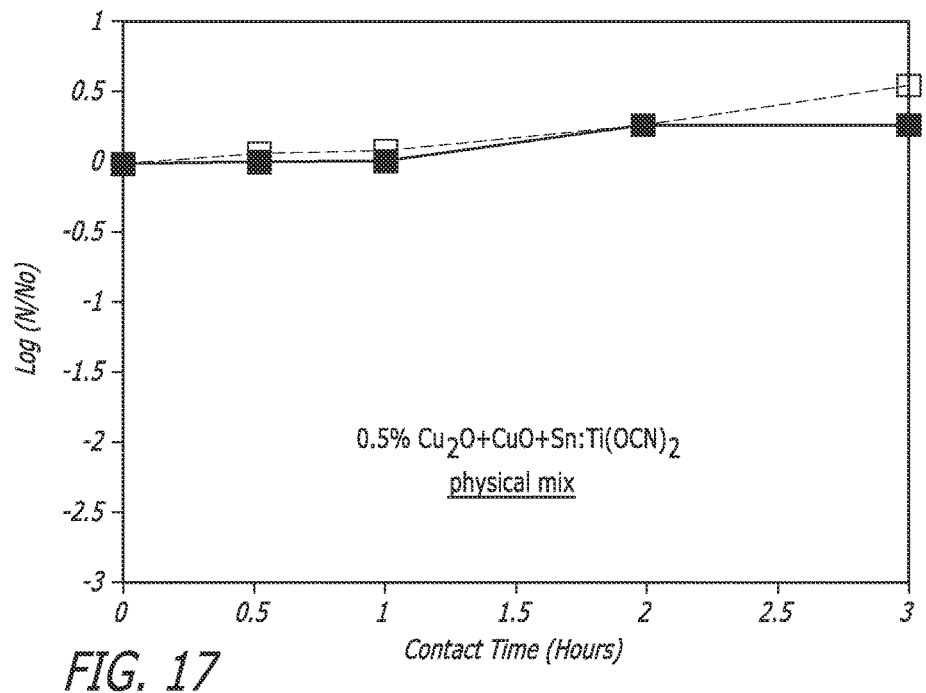
FIG. 17 is a graph showing the effect of a physical mixture of CE-0 (0.25 wt % CuO+0.12 wt % $Cu_2O$+0.5 wt % Sn doped $Ti(OCN)_2$ photocatalyst) on $E.\ coli$ killing property.
Figure 18:
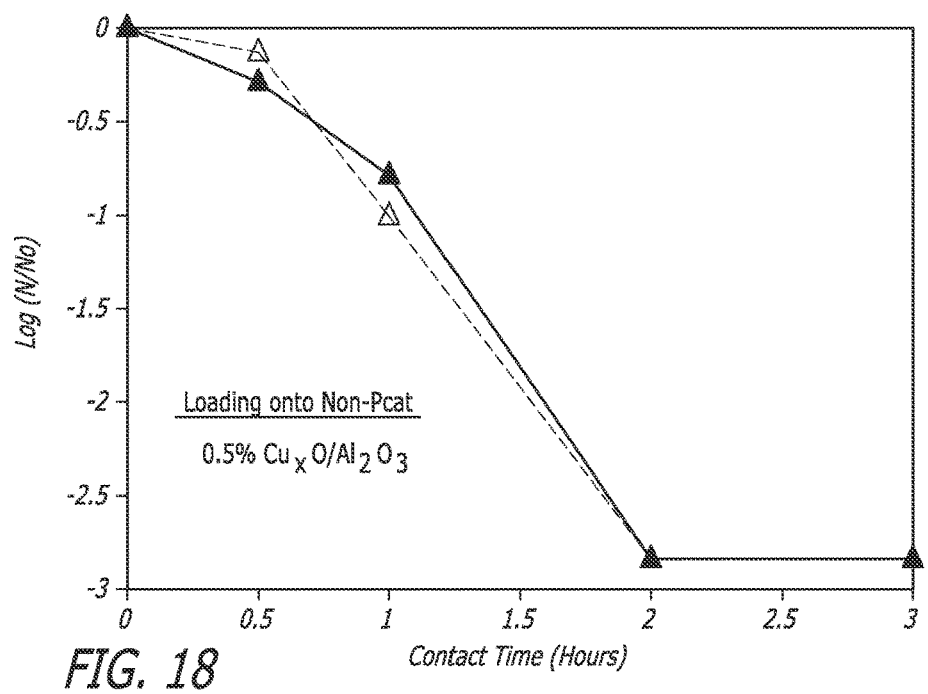
FIG. 18 is a graph showing the effect of Ex-7A (0.5 wt % $Cu_xO$ loaded alumina (non-photocatalyst)) on antibacterial property ($E.\ coli$ killing study).

The photocatalytic properties for Ex-18 ($Cu_xO$ loaded $MgTi_2O_5$) were examined by measuring the degradation of food additive dye (natural blue colored powder, Color Maker, Anaheim, Calif., USA) as natural blue color powder. The degradation was examined in the manner described in Example 5A. The results are shown in FIG. 17.

Example 6

Example 6(a). Photocatalysis Experiments for Antibacterial Studies 130 mg of each powdered sample (Examples 14-18 described above) was dissolved in a minimal amount of RO water (ca-15 mL) and homogenized for 5 min.

A clean petri dish was wiped with ethanol and the inside surface of the dish was ionized with a plasma device for 1 to 2 min. The homogeneous sample of each compound was poured into the treated petri dish and then heated at 120° C. while swirling to increase uniform distribution of the sample as it dried. After the sample had dried, the petri dish was placed under a UV Lamp (300 W) for 1 h. Each petri dish was then sealed in a separate 5 L Tedlar® bag under vacuum, followed by injecting 3 L of ambient air and 80 mL of 3500 ppm acetaldehyde. Each bag was lightly massaged for 2 min by hand then placed in the dark for 15 min. The acetaldehyde concentration was estimated by Gas Chromotagraphy-Flame Ionization Detector (GC-FID) to be at 80±2 ppm. Each Tedlar® bag containing a sample was placed back in the dark for 1 h. The slide/Tedlar® bag was exposed to array blue LED of 455 nm with light intensity of 0.656 mW/cm$^2$. A sample was collected every 30 min by an automated injection port of GC-FID and the amount of remaining acetaldehyde was estimated at subsequent 30 min intervals. The results are shown in Table 3 below.

TABLE 3

| Photocatalyst | % Acetylaldehyde lost after 5 h under BLED of 455 nm (0.656 mW/cm$^2$) |
|---|---|
| Bare GTP $WO_3$ (CE-6) | 38.84% |
| 0.05 mol % Pt on GTP $WO_3$ (EX-13) | 49.13% |
| 0.1 mol % Pt on GTP $WO_3$ (Ex-14) | 54.07% |

TABLE 3-continued

| Photocatalyst | % Acetylaldehyde lost after 5 h under BLED of 455 nm (0.656 mW/cm$^2$) |
|---|---|
| 0.1 mol % Ir GTP $WO_3$ (Ex-16) | 38.62% |
| 0.05 mol % Pt + 0.1 mol % Ir on GTP $WO_3$ (1$^{st}$ time) (Ex-17) | 64.46% |
| 0.05 mol % Pt + 0.1 mol % Ir on GTP $WO_3$ (2$^{nd}$ time) (Ex-17) | 63.38% |
| 0.05 mol % Pt + 0.1 mol % Ir on GTP $WO_3$ (3$^{rd}$ time) (Ex-17) | 59.52% |

Figure 14:
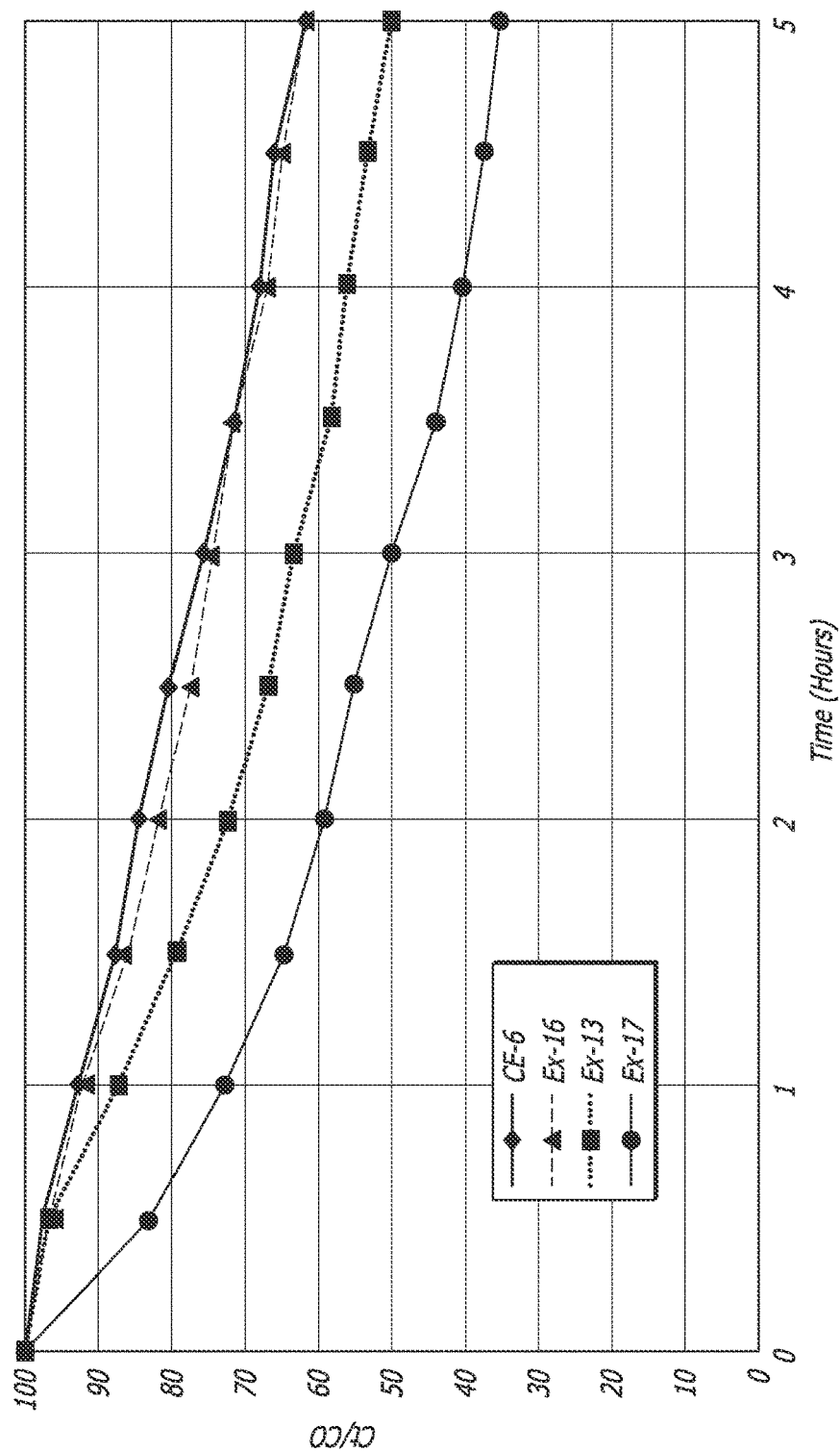
FIG. 14 is a graph showing the decomposition of acetaldehyde by various photocatalytic composites, Ex-12, 13, 15, 16 and CE-6 described herein.

FIG. 14 shows the decomposition rate of acetylaldehyde (Ct/Co) with $WO_3$ (commercial GTP) (CE-6), 0.05 mol % Pt loaded $WO_3$ (Ex-13), 0.1 mol % $IrO_2$ loaded $WO_3$ (Ex-16) and both 0.05 mol % Pt and 0.1 mol % $IrO_2$ loaded $WO_3$ (two times) (Ex-17). It is quite interesting to observe the results that Pt loading has a positive effect and $IrO_2$ alone loaded $WO_3$ has no effect on acetaldehyde decomposition under blue LED of 455 nm (0.656 mW/cm$^2$). However, when both Pt (0.05 mol %) and $IrO_2$ (0.1 mol %) loaded on $WO_3$ has resulted in further enhancement in the photodegradation of acetaldehyde under the same conditions when compared to that of Pt (0.05 mol %) alone or $IrO_2$ (0.1 mol %) alone or bare GTP $WO_3$ alone.

Example 6(b)

Figure 15:
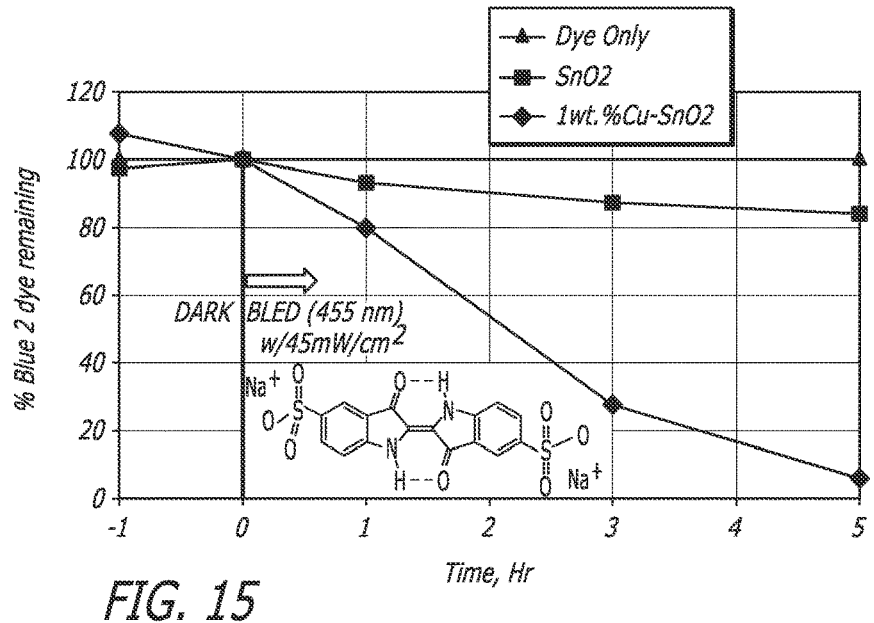
FIG. 15 is a graph showing the dye discoloration of blue dye color by various photocatalytic composites, Example 19 and $SnO_2$ without loading.

The photocatalytic properties for Ex-10 ($SnO_2$), CE-4A and food additive dye FD&C Blue No. 2 dye alone were compared by measuring the degradation of food additive dye FD&C Blue No. 2 dye (Synthetic blue colored powder, Chromatech, Inc, Michigan, USA). 2.85 g of the natural blue color powder was dissolved in 100 mL of RO water creating a blue powder stock solution. 150 mg of each sample was placed. The photocatalytic properties were determined in a manner described in Example 5a. The results are shown in FIG. 15.

Figure 16:
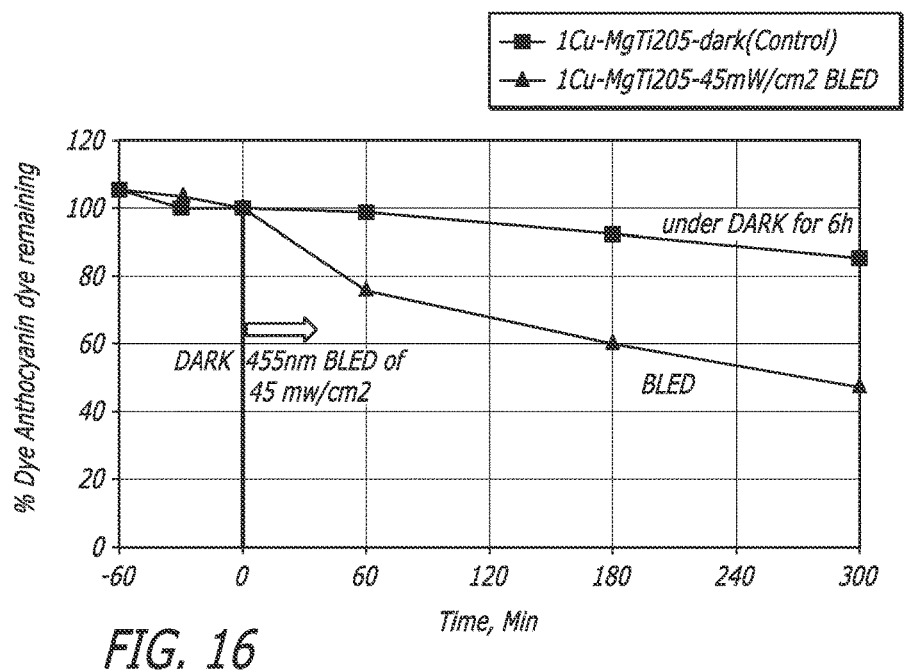
FIG. 16 is a graph showing the dye discoloration of natural blue color by various photocatalytic composites, Ex-18.

The photocatalytic properties for Ex-18 ($MgTiO_5$), and Ex-1 (SnTi $(OCN)_2$) loaded with $Cu_xO$ were compared by measuring the degradation of food additive dye FD&C Blue No. 2 dye (Synthetic blue colored powder, Chromatech, Inc, Michigan, USA). 2.85 g of the natural blue color powder was dissolved in 100 mL of RO water creating a blue powder stock solution. 150 mg of each sample was placed. The photocatalytic properties were determined in a manner described in Example 5a. The results are shown in FIG. 16.

Example 7

Example 7(a). Photocatalytic Inactivation of *E. coli* (ATCC 8739)

Method:

Substrate (1"×2" glass slide) was prepared by sequential application of 70% IPA (Isopropyl Alcohol), 100% EtOH and then dried in air. Ex-1B was dispersed in 100% EtOH at 2 mg/mL concentration and then about 100 μL of the suspension was applied to the substrate, and then dried. The application process was repeated 5 times to attain about 1 mg of Ex-1B on the substrate. The substrate was then dried at room temperature. The coated substrates were placed in a glass dish with a water soaked filter paper for maintaining moisture. Glass spacers were inserted between the substrates and the filter paper to separate the substrates from the filter paper.

Figure 19:
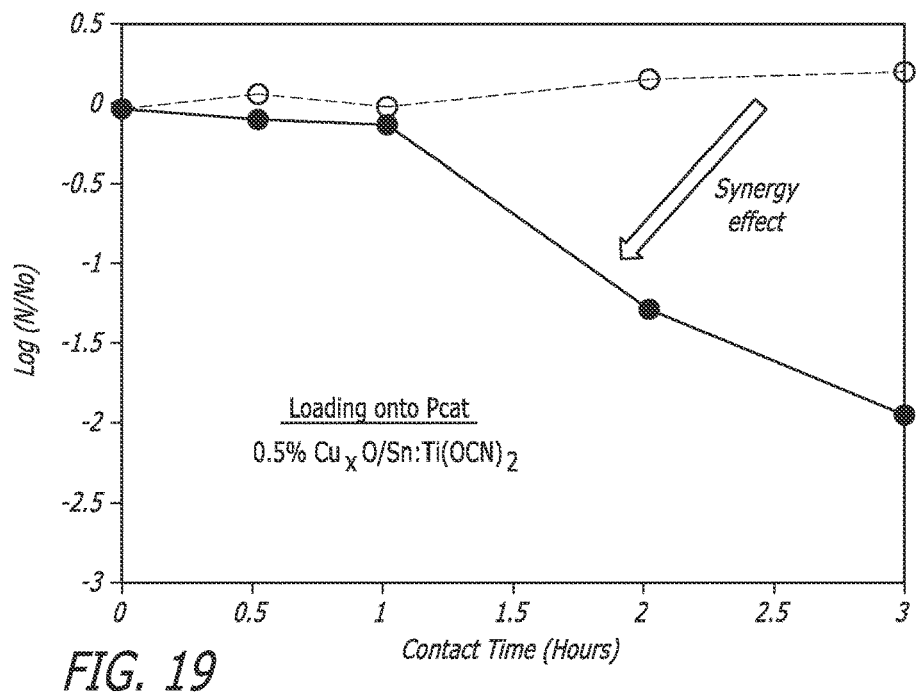
FIG. 19 is a graph showing the effect of Ex-1B (0.5 wt % $Cu_xO$ loaded Sn doped $Ti(OCN)2$ photocatalyst) on antibacterial property ($E.\ coli$ killing study).

E. coli (ATCC 8739) was streaked onto a 5 cm diameter petri dish containing about 25 ml of LB agar, and incubated at about 37° C. overnight. For each experiment, a single colony was picked to inoculate about 3 mL nutrient broth, and the inoculated culture was incubated at about 37° C. for about 16 h to create an overnight culture (~$10^9$ cells/mL). A fresh log-phase culture of the overnight culture was obtained by diluting the overnight culture 100×, inoculating another 5 cm petri dish with LB agar and then incubated at about 37° C. for about 2.5 h. The fresh culture was diluted 50×, which gave a cell suspension of about $2 \times 10^6$ cells/mL. 50 µL of the cell suspension was pipetted onto each glass substrate. A sterilized (in 70% and then 100% EtOH) plastic film (20 mm×40 mm) was placed over the suspension to spread the suspension evenly under the film. At chosen time point, e.g., about 30 min increments, the specimen was placed in 10 mL of 0.85% saline and vortexed at 3200 rpm for about 1 min to wash off the bacteria. The wash off suspension was serially diluted using 0.85% saline, and plated on LB agar and incubated at about 37° C. overnight to determine the number of viable cells in terms of CFU/Specimen. Counting was performed by visual inspection and the result multiplied by the dilution factor to arrive at the determined number. The specimen was then irradiated and positioned under a 455 nm blue light emitting LED to provide about 45 mw/cm$^2$ to the specimen. The results are shown in FIG. 19.

The anti-bacterial properties of CE-7 and Ex-7A were determined as described in Example 6A, except that molar equivalent amounts of CE-7 and Ex-7A were used instead of Ex-1B. The results are shown in FIGS. 17 (CE-7) and 18 (Ex-7A).

Figure 20:
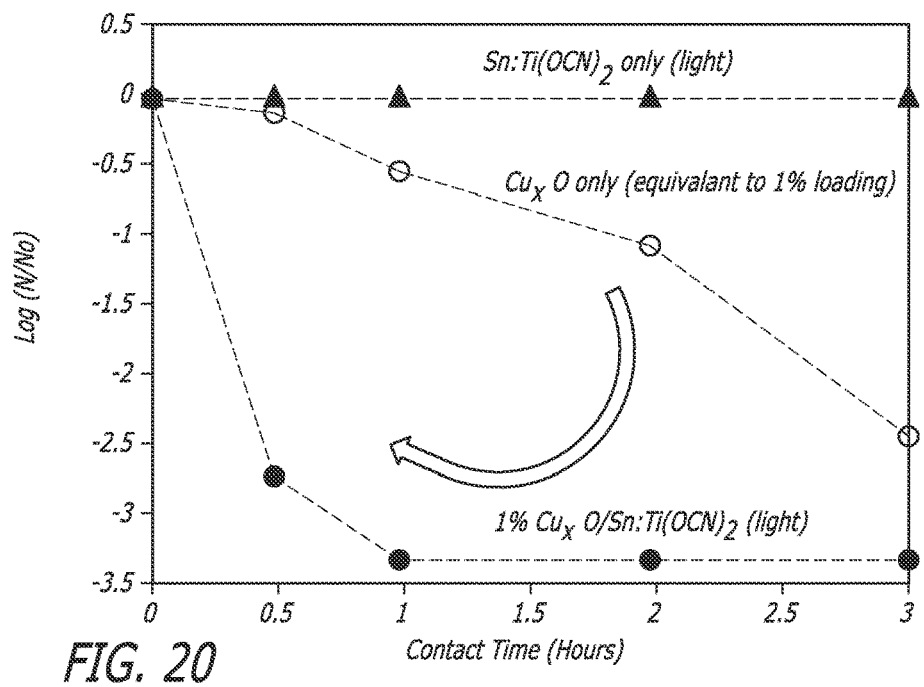
FIG. 20 is a graph showing the synergy effect of Ex-1 (1 wt % $Cu_xO$ loaded Sn doped $Ti(OCN)_2$) on antibacterial property ($E.\ coli$ killing study).
Figure 21:
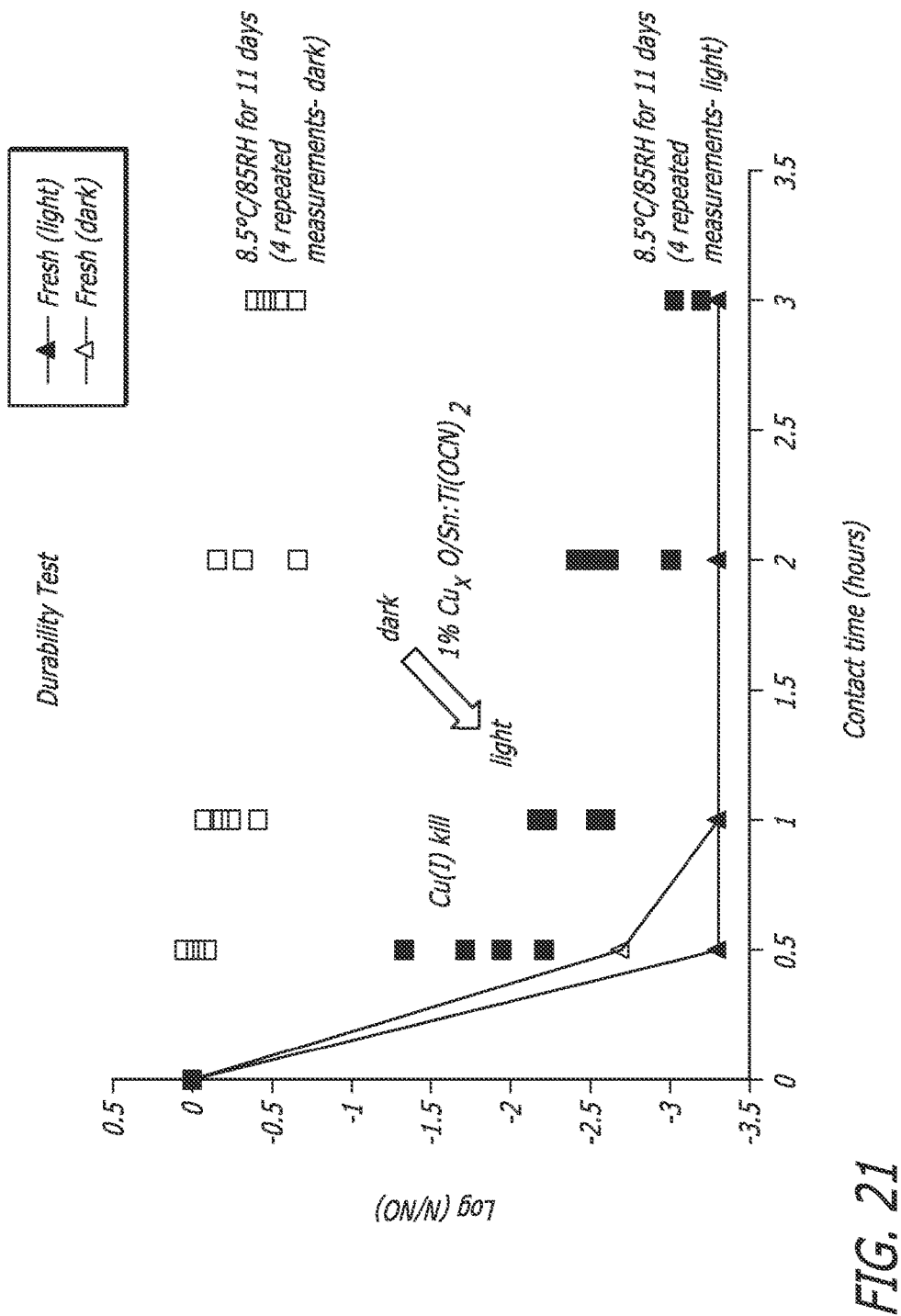
FIG. 21 is a graph showing the enhanced durability result of Ex-1 (1 wt % $Cu_xO$ loaded Sn doped $Ti(OCN)_2$) on antibacterial property ($E.\ coli$ killing study).

The antibacterial properties of Ex-1 (loaded 1% Cu$_x$O/Sn:Ti(OCN)$_2$), Cu$_x$O only and unloaded Sn:Ti(OCN)$_2$ (as described in Example 1(a)) were compared by measuring the antibacterial activity as described in Example 6A. The results are shown in FIG. 20.

Example 7(b). Function of Pcat I 50 mg of Cu$_x$O/P25™ (as produced in Example 1(m)) was mixed with 1 mL of 10% bleach (Clorox Germincidal, NaClO based) in a 1.6 mL Eppendorf® centrifuge tube, and incubated at room temperature (~24° C.) for 2 h, with shaking (setting 9 on an analog VWR® vortex). After incubation, the tube was centrifuged in an Eppendorf® 5430 micro-centrifuge (2 min at 14167 rcf), after which the particles formed a solid pellet at the bottom of the tube. The clear supernatant was carefully removed, and 1 mL of DI water was added. The tube was vortexed until the pellet was fully disrupted and the suspension became homogeneous. It was then centrifuged again. This process was repeated four more times.

After the final centrifugation, the pellet was resuspended in 1 mL of DI water and mixed with 4 mL of DI water in a 20 mL clear glass vial with lid. 5 mL of methanol was added, bringing the total volume in the vial to ~10 mL.

A magnetic stir bar (½"×⅛", disposable) was added to the vial, and placed on a stir plate (1000 rpm). The vial was irradiated using a A300W™ Xenon lamp (Oriel® 68811) placed about 15 cm away from the vial wall. The irradiation lasted 1 h in a vented hood, and there was negligible temperature change in the vial during the process.

After irradiation, the content of the vial was centrifuged to remove all the liquid. The pellet was dried in vacuum, and resuspended in 25 mL of 200 proof EtOH. The mixture was then sonicated in a sonicator for 20 min.

100 mL of the sonicated dispersion was spread evenly on one side of a 1"×2" glass slide. After the surface was dry (in a vented hood), the process was repeated, for a total of five coatings. The coated slide was then used in a standard bacterial test. A schematic of the experimental procedure used in Example 7(b) is shown in the top panel of FIG. 22.

For the control, 50 mg of Cu$_x$O/Al$_2$O$_3$ was treated in the same manner as above, and was then used to make coated slides. These control slides were subjected to the standard bacterial test in the same manner as Cu$_x$O/P25™. The antibacterial effects results from samples taken from Steps (1), (2), and (3) from the dark tests were plotted in the lower panel of FIG. 22.

Figure 22:
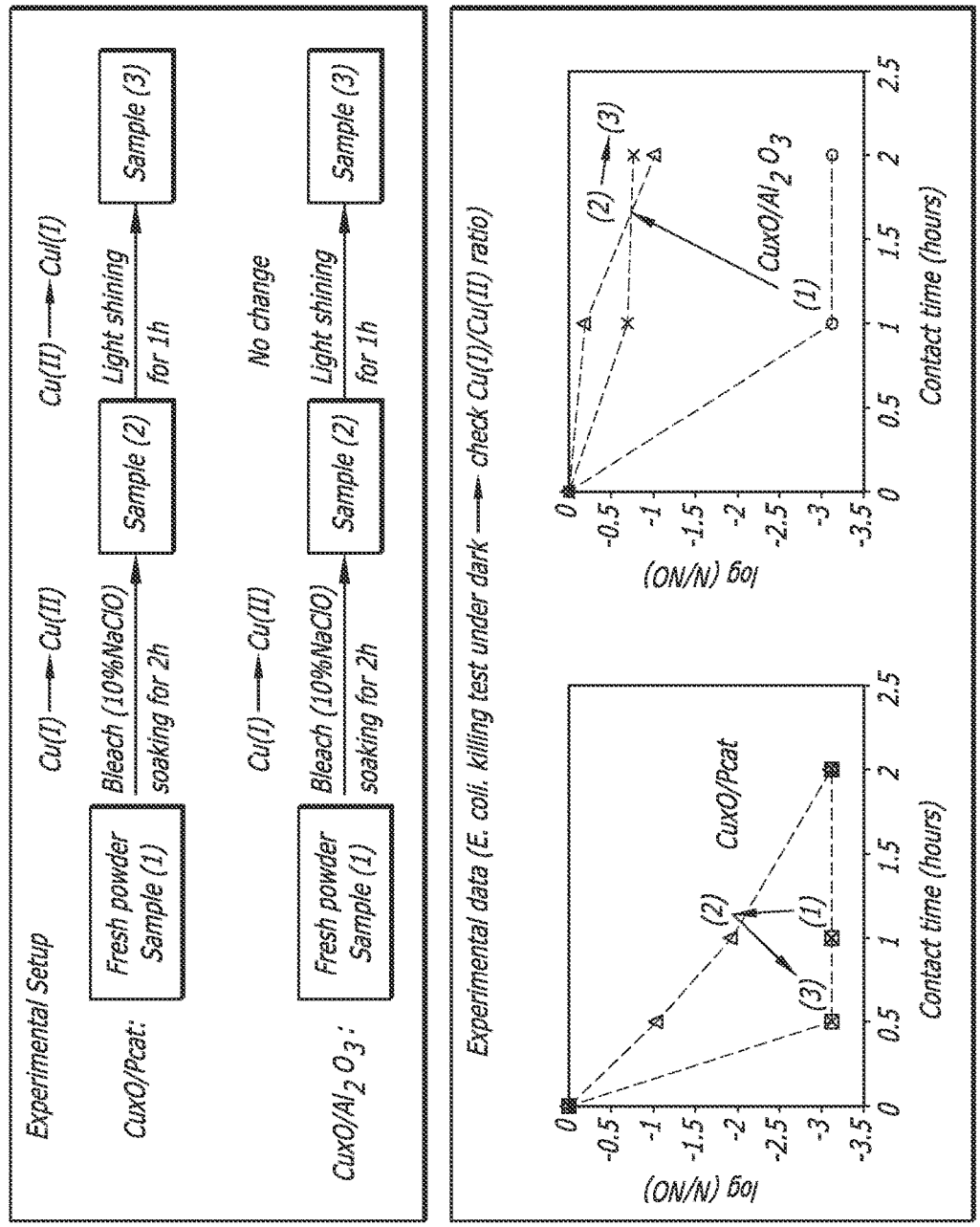
FIG. 22 shows a schematic of the experimental procedure and graphs showing the synergy effect of $Cu_xO$/P25 and $Cu_xO/Al_2O_3$ for antibacterial properties ($E.\ coli$ killing study).

As shown in the FIG. 22 (lower panel, left plot), the freshly prepared Cu$_x$O/P25™ sample (1) showed a high antibacterial activity, reducing the E. coli concentration by 3 log units after 30 min in darkness. The bleach-treated CuxO/P25™ sample (2) did not show as much antibacterial activity as sample (1), only achieving 3 log E. coli reduction after 2 hours in darkness. Sample (3) showed antibacterial activity comparable to an untreated sample (1), also achieving 3 log E. coli reduction in 30 min.

In contrast, the Cu$_x$O/Al$_2$O$_3$ sample (3) did not show as high of an antibacterial function after irradiation (FIG. 22, lower panel, right plot). The Cu$_x$O/Al$_2$O$_3$ bleach treated/irradiated sample (3) showed a similar antibacterial activity to that of the bleach treated only Cu$_x$O/Al$_2$O$_3$ sample (2). However, both Cu$_x$O/Al$_2$O$_3$ samples (2) and (3) were significantly lower than that of the freshly prepared Cu$_x$O/Al$_2$O$_3$ sample (1).

Example 7(c). Function of Pcat II

To investigate how the duration of bleach treatment affected the activity of the copper oxide loaded material, the above experiments of Example 7(b) were carried out with the bleach treatment duration set for 2 and 16 h. All other aspects of the experiment remained the same. A schematic of the experimental procedure is shown in FIG. 23, top panel.

Figure 23:
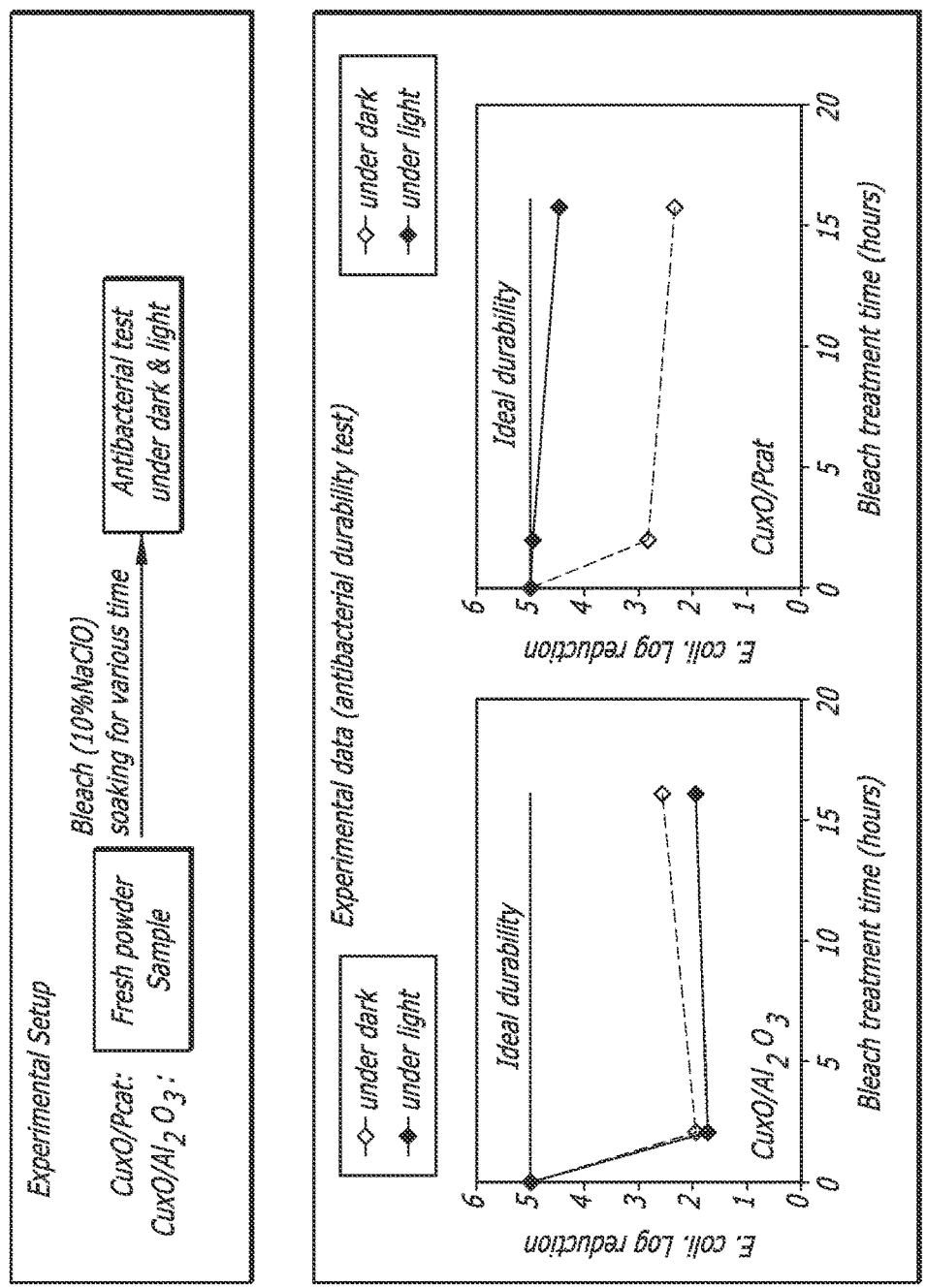
FIG. 23 shows a schematic of the experimental procedure and graphs showing the enhanced durability result of $Cu_xO$/P25™ and $Cu_xO/Al_2O_3$ for antibacterial properties ($E.\ coli$ killing study).

The *E. coli* concentration log reduction results from these treated samples were plotted together with that from untreated material in FIG. 23, lower panel.

In FIG. 23, (lower panel, left plot), bleach treatment of $Cu_xO/Al_2O_3$ led to significant drop of dark antibacterial activity. Tests under light conditions were not able to restore activity to any great extent. In contrast, $Cu_xO/Pcat$ (P25™) (FIG. 23, lower panel, right plot), had similar dark antibacterial activity, however, light antibacterial activity was restored. After 16 h of bleach treatment, the antibacterial light activity was still largely intact which demonstrates the durability of $Cu_xO/P25$™ as an antibacterial agent.

Aqueous Combustion Synthesis of Boron Doped $WO_3$

Aqueous combustion method was used to prepare boron-doped $WO_3$ with Epsilon Phase.

5 mg ammonium metatungstate hydrate (Inframat Advanced Materials, Manchester, Conn., USA), 100 mg boric acid (Sigma-Aldrich, St. Louis Mo., USA), 2 g carbohydrazide (Sigma-Aldrich), and 10 g ammonium nitrate (Sigma-Aldrich) were dissolved in 50 ml of DI water. The aqueous solution was then place in a muffle furnace, preheated to about 420° C. until combustion was substantially completed (for about 20 min). After the combustion was over, the product was annealed in air at about 425° C. for about 30 min. The body color of the powder appeared orange-yellow in color and was confirmed by comparison with powder XRD pattern with a standard epsilon $WO_3$ x-ray diffraction (ICFF PDF card number 01-087-2404)

Example 7(d). Surface Modification of Epsilon $WO_3$ by Strong and Selective Adsorption Method Using Cobalt Oxide 1 μm of epsilon $WO_3$ and 40.37 g of $CoCl_2.4H_2O$ were dissolved in about 10 mL DI water and stirred at about 90° C. for about 2 h in a 40 mL closed vial reactor. Then, the closed vial reactor was quenched in tap water and filtered through a membrane filter [fine to 0.05 μm], washed with DI water several times (at least about 250 ml) and dried at about 110° C. for about 2 h resulting in cobalt oxide loaded epsilon $WO_3$.

Example 8

Example 8(a). Acoustic Mixing of Two Different N-Type Semiconductors $WO_3$ (12 g), one n-type semiconductor was uniformly mixed with another n-type semiconductor ($CeO_2$ (8 g)) in an acoustic mixer for about 5 min at the acceleration of 45-50 GHz in a plastic container.

Example 8(b). Hydrothermal Loading of $Cu_xO$ on $WO_3+CeO_2$ Mixture

About 1 g of the $WO_3/CeO_2$ acoustically-mixed powder was put in a 20 mL Teflon™-lined stainless steel container along with various amounts of copper-bis-ethylene-diaminedihydroxide ($Cu(EN)_2(OH)_2$)(1M aqueous solution) with 10 mL of Milli-Q® water as described in Table 1. Table 1 summarizes the three different compositions synthesized by hydrothermal $Cu_xO$ loading on a mixture of ($WO_3+CeO_2$).

TABLE 1

| Pre-mixture amount | Volume of Milli-Q® $H_2O$ | Volume of $Cu(EN)_2(OH)_2$ (1M) | Loading Temperature | Drying conditions | Nominal composition |
|---|---|---|---|---|---|
| 1 g | 10 mL | 0.08 mL | 110° C./15 h | 110° C./2 h | 0.5 wt % ratio |
| 1 g | 10 mL | 0.016 mL | 110° C./15 h | 110° C./2 h | 0.1 wt % ratio |
| 1 g | 10 mL | 0.008 mL | 110° C./15 h | 110° C./2 h | 0.05 wt % ratio |

The $WO_3/CeO_2$ aqueous mixture was heated in a Teflon™-lined stainless steel autoclave at about 110° C. for about 15 h under autogenous pressure while in a sealed container. The products were consecutively filtered and washed with water through a 0.05 μm pore membrane filter paper. The products, along with the filter paper, were then dried at 110° C. in an air-oven for about 2 h.

Example 9

Example 9(a). Acoustic Mixing of Two Different N-Type Semiconductors $WO_3$ (12 g), one n-type semiconductor is uniformly mixed with another n-type semiconductor ($TiO_2$, anatase (4.14 g)) in an acoustic mixer for about 5 min. at the acceleration of 45-50 GHz in a plastic container.

Example 9(b). Hydrothermal Loading of $Cu_xO$ on $WO_3+TiO_2$ Mixture

About 1 g the $WO_3/TiO_2$ acoustically mixed powder was put in a 20 mL Teflon™-lined stainless steel container along with various amounts of $Cu(EN)_2(OH)_2$ (1M aqueous solution) with 10 mL of Milli-Q® water as described in Table 2. Table 2 summarizes the three different compositions prepared by hydrothermal $Cu_xO$ loading on the mixture of ($WO_3+TiO_2$).

TABLE 2

| Pre-mixture amount | Volume of Milli-Q® $H_2O$ | Volume of $Cu(EN)_2(OH)_2$ (1M) | Loading Temperature | Drying conditions | Nominal composition |
|---|---|---|---|---|---|
| 1 g | 10 mL | 0.08 mL | 110° C./15 h | 110° C./2 h | 0.5 wt % ratio |
| 1 g | 10 mL | 0.016 mL | 110° C./15 h | 110° C./2 h | 0.1 wt % ratio |
| 1 g | 10 mL | 0.008 mL | 110° C./15 h | 110° C./2 h | 0.05 wt % ratio |

The WO$_3$/TiO$_2$ aqueous mixture was heated in a Teflon™-lined stainless steel autoclave at 110° C. for 15 h under autogenous pressure. The products were consecutively filtered and washed with water through a 0.05 μm pore membrane filter paper. The products, along with filter paper, were then dried at 110° C. in an air-oven for about 2 h.

Example 10

Example 10(a). Acoustic Mixing of Two Different N-Type Semiconductors

WO$_3$ (3.2 g), one n-type semiconductor is uniformly mixed with another n-type semiconductor (GeO$_2$, (1.4 g)) (1:1 molar ratio) in a vortex mixer for about 5 min in a 20 mL glass vial.

Example 10(b). Hydrothermal Loading of Cu$_x$O on WO$_3$+GeO$_2$ Mixture

About 1 g of the WO$_3$/GeO$_2$ acoustically mixed powder was put in a 20 mL Teflon-lined stainless steel container along with various amounts of Cu(EN)$_2$(OH)$_2$ (1M aqueous solution) with 10 mL of Milli-Q® water as described in Table 3. Table 3 summarizes the three different compositions prepared by hydrothermal Cu$_x$O loading on the mixture of (WO$_3$+GeO$_2$).

TABLE 3

| Pre-mixture amount | Volume of Milli-Q® H$_2$O | Volume of Cu(EN)$_2$(OH)$_2$ (1M) | Loading Temperature | Drying conditions | Nominal composition |
|---|---|---|---|---|---|
| 1 g | 10 mL | 0.08 mL | 110° C./15 h | 110° C./2 h | 0.5 wt % ratio |
| 1 g | 10 mL | 0.016 mL | 110° C./15 h | 110° C./2 h | 0.1 wt % ratio |
| 1 g | 10 mL | 0.008 mL | 110° C./15 h | 110° C./2 h | 0.05 wt % ratio |

The WO$_3$/GeO$_2$ aqueous mixture was heated in a Teflon™-lined stainless steel autoclave at 110° C. for 15 h under autogenous pressure. The products were consecutively filtered and washed with water through a 0.05 μm pore membrane filter paper. The products, along with filter paper, were dried at 110° C. in an air-oven for about 2 h.

Example 11

Hydrothermal Loading of Cu$_x$O on WO$_3$+ZrO$_2$ Mixture

About 1 g of powder mixture (65% WO$_3$ and 35% ZrO$_2$ by weight) from the acoustic mixer was put in a 20 mL Teflon™-lined stainless steel container along with various amounts of Cu(EN)$_2$(OH)$_2$ (1M aqueous solution) in total of 10 mL of Milli-Q® water as described in Table 4. Table 4 summarizes the three different compositions prepared by hydrothermal Cu$_x$O loading on the mixture of (WO$_3$+ZrO$_2$). (RENECAT, Toshiba, Osaka, Japan).

TABLE 4

| Pre-mixture amount | Volume of Milli-Q® H$_2$O | Volume of Cu(EN)$_2$(OH)$_2$ (1M) | Loading Temperature | Drying conditions | Nominal composition |
|---|---|---|---|---|---|
| 1 g | 10 mL | 0.08 mL | 110° C./15 h | 110° C./2 h | 0.5 wt % ratio |
| 1 g | 10 mL | 0.016 mL | 110° C./15 h | 110° C./2 h | 0.1 wt % ratio |
| 1 g | 10 mL | 0.008 mL | 110° C./15 h | 110° C./2 h | 0.05 wt % ratio |

The WO$_3$/ZrO$_2$ aqueous mixture was heated in a Teflon™-lined stainless steel autoclave at 110° C. for 15 h under autogenous pressure. The products was consecutively filtered and washed with water through a 0.05 μm pore membrane filter paper. The products, along with filter paper, were dried at 110° C. in an air-oven for about 2 h.

Example 12

Example 12(a). Pre-Treatment for Photocatalysis 130 mg of each powdered samples from Examples 8 was dispersed in a minimal amount of reverse-osmosis purified (RO) water (Ca. 1.5 mL) and homogenized for about 5 min in a bath sonication.

A clean petri dish was wiped with ethanol and the inside surface of the dish was ionized with a plasma device for 1 to 2 min. The homogeneous sample of each compound was poured into the treated petri dish and then heated at 120° C. while swirling to increase uniform distribution of the sample as it dried. After the sample had dried, the petri dish was placed under a UV Lamp (300 W) for 1 h.

Example 12(b). Photocatalysis Evaluation

Figure 24:
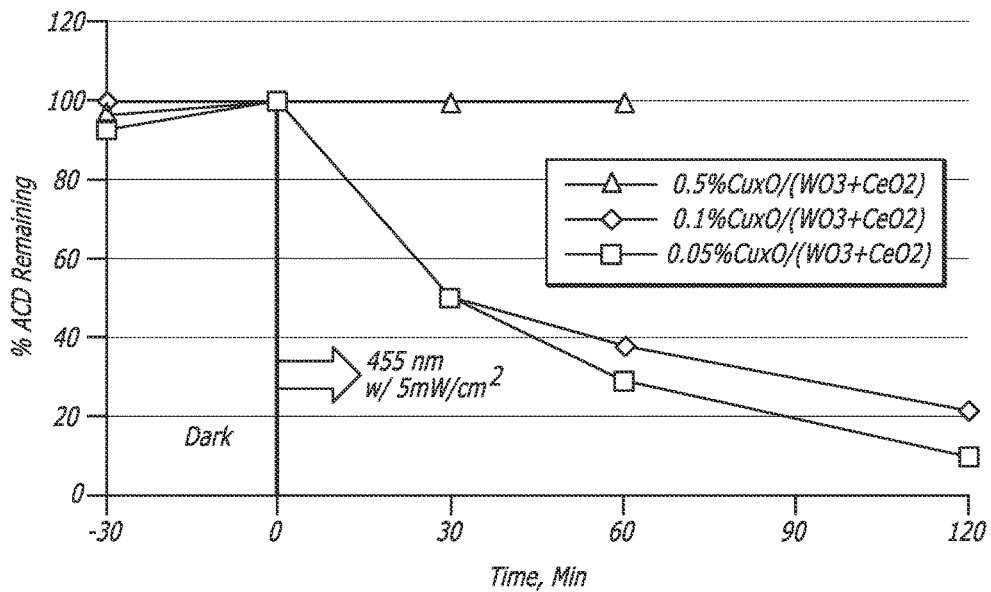
FIG. 24 is a plot of % acetaldehyde degradation over time using various concentrations of heterogeneous materials as photocatalysts.
Figure 25:
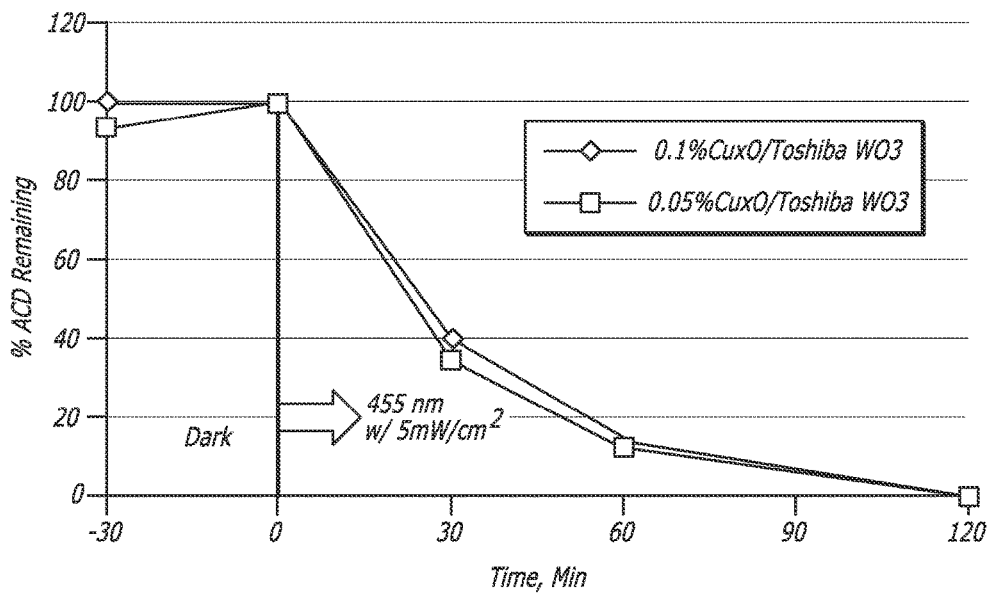
FIG. 25 is a plot of % acetaldehyde degradation over time using various concentrations of heterogeneous materials as photocatalysts.

The petri dish was then sealed in a separate 5 L Tedlar® bag, followed by injecting 3 L of ambient air and 70 mL of 3500 ppm acetaldehyde. Each bag was lightly massaged for 2 min by hand then placed in the dark for 15 min. The acetaldehyde concentration was estimated by GASTEC™ Tube (92M). The Tedlar® bag containing a sample was placed back in the dark for 30 min. The Tedlar® bag was exposed to blue LED of 455 nm with light intensity of 5 mW/cm$^2$. A sample was collected at 30 min, 60 min and 120 min. The activity results are summarized in FIGS. 24 and 25.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

The terms "a," "an," "the" and similar referents used in the context of describing the invention (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of any claim. No language in the specification should be construed as indicating any non-claimed element essential to the practice of the invention.

Groupings of alternative elements or embodiments disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, the claims include all modifications and equivalents of the subject matter recited in the claims as permitted by applicable law. Moreover, any combination of the above-described elements in all possible variations thereof is contemplated unless otherwise indicated herein or otherwise clearly contradicted by context.

In closing, it is to be understood that the embodiments disclosed herein are illustrative of the principles of the claims. Other modifications that may be employed are within the scope of the claims. Thus, by way of example, but not of limitation, alternative embodiments may be utilized in accordance with the teachings herein. Accordingly, the claims are not limited to embodiments precisely as shown and described.

What is claimed is:

1. A heterogeneous material comprising:
a p-type semiconductor comprising a first metal oxide compound and a second metal oxide compound, wherein the first metal oxide compound and the second metal oxide compound have different oxidation states of the same metal, and wherein the p-type semiconductor has a p-type valence band;
a first n-type semiconductor having an n-type valence band which is deeper than the p-type valence band, wherein the first n-type semiconductor is in ionic charge communication with the p-type semiconductor, and wherein the n-type semiconductor comprises 90 to 99.999 wt % of the heterogeneous material.

2. The heterogeneous material of claim 1, further comprising a second n-type semiconductor.

3. The heterogeneous material of claim 1, wherein the first n-type semiconductor is $TiO_2$.

4. The heterogeneous material of claim 1, wherein the first n-type semiconductor is a combination of anatase $TiO_2$ and rutile $TiO_2$.

5. The heterogeneous material of claim 1, wherein the first n-type semiconductor comprises $WO_3$.

6. The heterogeneous material of claim 2, wherein the molar ratio of the first n-type semiconductor to the second n-type semiconductor is about 0.5 to about 10.

7. The heterogeneous material of claim 2, wherein the second n-type semiconductor is $CeO_2$, $GeO_2$, $SnO_2$, or $ZrO_2$.

8. The heterogeneous material of claim 2, wherein the second n-type semiconductor is $CeO_2$.

9. The heterogeneous material of claim 2, wherein the second n-type semiconductor is $GeO_2$.

10. The heterogeneous material of claim 2, wherein the second n-type semiconductor is $SnO_2$.

11. The heterogeneous material of claim 1, wherein the p-type semiconductor comprises $Cu_xO$.

12. The heterogeneous material of claim 1, wherein the p-type semiconductor is about 0.001% to about 5% of the heterogeneous material by weight.

13. The heterogeneous material of claim 1, wherein the p-type semiconductor is $Cu_xO$, and is about 0.01% to about 1% of the heterogeneous material by weight.

14. A heterogeneous material comprising:
a p-type semiconductor comprising a first metal oxide compound and a second metal oxide compound, wherein the first metal oxide compound and the second metal oxide compound have different oxidation states of the same metal, and wherein the p-type semiconductor has a p-type valence band;
a first n-type semiconductor having an n-type valence band which is deeper than the p-type valence band, wherein the first n-type semiconductor is in ionic charge communication with the p-type semiconductor;
a second n-type semiconductor;
wherein at least 50% of the p-type semiconductor is loaded onto the surface of particles of the first n-type semiconductor and particles of the second n-type semiconductor.

15. A heterogeneous material comprising:
a p-type semiconductor comprising a first metal oxide compound and a second metal oxide compound, wherein the first metal oxide compound and the second metal oxide compound have different oxidation states of the same metal, and wherein the p-type semiconductor has a p-type valence band;
a first n-type semiconductor having an n-type valence band which is deeper than the p-type valence band, wherein the first n-type semiconductor is in ionic charge communication with the p-type semiconductor;
wherein the heterogeneous material is in the form of a powder.

16. A method of preparing a heterogeneous material comprising:
heating a mixture of:
1) a first n-type semiconductor and a second n-type semiconductor; and
2) an aqueous solution comprising a copper ion complex;
wherein the first n-type semiconductor and the second n-type semiconductor are mixed prior to combining the first n-type semiconductor and the second n-type semiconductor with the aqueous solution comprising the copper ion complex as a precursor of a p-type semiconductor;

wherein the copper ion complex comprises copper ions have at least two different oxidation states, and wherein the complex has a p-type valence band;

wherein the first and second n-type semiconductors have an n-type valence band which is deeper than the p-type valence band; and wherein the copper ion complex comprises 0.001 to 10 wt % of the heterogeneous material.

17. The method of claim 16, further comprising filtering the heterogeneous material out of the mixture of the after the mixture has been heated.

18. A method of decomposing a chemical compound, comprising exposing the chemical compound to a photocatalyst comprising the heterogeneous material of claim 1 in the presence of light.

19. The method of claim 18, wherein the chemical compound is a pollutant.

20. A method of killing a microbe, comprising exposing the microbe to a photocatalyst comprising the heterogeneous material of claim 1 in the presence of light.

\* \* \* \* \*